United States Patent [19]
Rossignol et al.

[11] Patent Number: 5,952,309
[45] Date of Patent: *Sep. 14, 1999

[54] METHOD FOR TREATING ALCOHOLIC LIVER DISEASE

[75] Inventors: Daniel P. Rossignol, Andover, Mass.; Ronald G. Thurman, Chapel Hill, N.C.; William J. Christ; Michael D. Lewis, both of Andover, Mass.

[73] Assignee: Eisai Company, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/720,131

[22] Filed: Sep. 27, 1996

Related U.S. Application Data

[60] Provisional application No. 60/004,577, Sep. 29, 1995, and provisional application No. 60/004,795, Oct. 2, 1995.

[51] Int. Cl.⁶ .................................................. A61K 31/70
[52] U.S. Cl. .............................. 514/25; 514/53; 514/893
[58] Field of Search .................................. 514/25, 53, 893

[56] References Cited

U.S. PATENT DOCUMENTS

| | | | |
|---|---|---|---|
| 5,413,785 | 5/1995 | Nanji | 424/93.45 |
| 5,530,113 | 6/1996 | Christ et al. | 536/123.13 |

FOREIGN PATENT DOCUMENTS

| | | |
|---|---|---|
| 0 536 969 | 4/1993 | European Pat. Off. . |

OTHER PUBLICATIONS

Nolan, J. P. *Immunological Investigations* 1989, 18, 325–327. Month not available.
Nolan, J. P. *Hepatology* Nov. 1989, 10, 887–889.
Adachi et al. *Hepatology* Aug. 1994, 20, 453–460.
Adachi et al., *Gastroenterology*, 108:218–224, 1995.
Adachi et al., *J. Hepatol.*, 20: 453–460, Aug. 1994.
Bone, *Chest*, 100:802–808, Sep. 1991.
Casteleijn et al., *J. Bio. Chem.*, 263:2699–2703, Feb. 1988.
DeCarli et al., *J. Nutr.*, 91:331–336, Mar. 1967.
Decker et al., *Cells of the Hepatic Sinusoid*, pp. 171–175, 1989.
Felver et al. *Alcohol Clin. Exp. Res.*, 14:255–259, Mar./Apr. 1990.
Freudenberg et al., *British J. of Exp. Path.* 63:56–64, 1982.
Galanos et al., *Proc. Nat'l. Acad. Sci.*, 76:5939–5943, Nov. 1979.
Goto et al., *J. Pharmacol. Exp. Ther.*, 267:1264–1268, 1993.
Grynkiewicz et al., *J. Bio. Chem.*, 260:3440–3450, Mar. 1985.
Hijioka et al., *Mol. Pharmacol.*, 41:435–440, 1992.
Iwaki et al., *Cells of the Hepatic Sinusoid*, pp. 351–352, 1989.
Karck et al., *Cells of the Hepatic Sinusoid*, pp. 210–211, 1989.
Knecht et al., *Mol. Pharmacol.*, 47:1028–1034, 1995.
Lahnborg et al., *Scand. J. Gastroent.*, 16:481–489, 1981.
Laskin, *Cells of the Hepatic Sinusoid*, pp. 284–287, 1989.
Lelbach, *Acta Hepatospenol.*, 13:321–349, Nov./Dec. 1966.
Martinez et al., *Alcohol*, 9:455–458, 1992.
Marzi et al., *Transplant Proc.*, 22:2004–2005, Aug. 1990.
Mathison et al., *J. Immunol.*, 123:2133–2143, Nov. 1979.
Mendelson et al., *Anns. NY Acad. Sci.*, 133:828–845, 1966.
Monden et al., *Res. Exp. Med.*, 191:177–187, 1991.
Nanji et al., *Ame. J. Pathol.*, 142:367–373, Feb. 1993.
Nolan, *Hepatology*, 1:458–465, 1981.
Pertoft et al., *Cell Separation*, 4:1–24, 1987.
Porta et al., *Lab Invest.*, 18:352–364, 1968.
Rose et al., *Inf. and Immun.*, 63:833–839, Mar. 1995.
Ruiter et al., *Lab Invest.*, 45:38–45, 1981.
Shiratori et al., *Cells of the Hepatic Sinusoid*, pp. 313–318, 1989.
Thurman et al., *Proc. 78th Falk Symposium*, pp. 185–203, 1995.
Thurman et al., *Molecular Pharmacol.*, 12:156–166, 1975.
Ueno et al., *Cells of the Hepatic Sinusoid*, 2:293–296, 1989.
Van Bossuyt et al., *Cell Tiss. Res.*, 251:205–215, 1988.
Vogel et al., *J. Immunol.*, 124:2004–2009, Apr. 1980.
Wisse et al., *Cells of the Hepatic Sinusoid*, 2:1–8, 1989.
Yamada et al., *Liver*, 11:220–224, 1991.
Yuki et al., *Biochem. J.*, 186:119–126, 1980.

*Primary Examiner*—Kathleen K. Fonda
*Attorney, Agent, or Firm*—Darby & Darby

[57] ABSTRACT

A method for the inhibition and amelioration of alcholic liver disease in a mammal in need of such treatment by administering novel analogs of Lipid A which act as endotoxin antagonists. These antagonists compounds are found to inhibit the swift increase in alcohol metabolism which typically accompanies ingestion of alcohol and which may lead to the pathophysiological abnormalities associated with alcoholic liver disease.

17 Claims, 5 Drawing Sheets

METHOD FOR TREATING ALCOHOLIC LIVER DISEASE

This application claims priority from U.S. provisional application Ser. Nos. 60/004,577, filed Sep. 29, 1995, and 60/004,795, filed Oct. 2, 1995.

BACKGROUND OF THE INVENTION

Alcoholic liver disease is a progressive disease with approximately 600,000 new cases a year world-wide. The incidence of mortality from this disease is high (e.g. it is the fourth leading cause of death in U.S. urban males), and current effective treatments are nonexistent except for drastic measures such as liver transplantation.

Often a consequence of alcoholic liver disease, cirrhosis follows deposition of fatty and fibrous tissue in the liver with diffuse damage to the hepatic parenchymal cells. Loss of proper metabolic functioning in these cells leads to interference with liver blood flow, jaundice, portal hypertension, ascites, and hepatic failure.

While it is well recognized that alcohol consumption leads to liver disease, the exact mechanism(s) by which alcohol exerts its toxic effect remains unclear (Lelbach, W. K. Acta Hepatospenol. 13: 321–349 (1966)). One hypothesis which the present inventors have investigated implicates an interactive toxicity between alcohol and endotoxin (Adachi et al. J Hepatol, 16: 171–176. (1992), Adachi, Y. et al. Hepatol. 20: 453–460 (1994), Knecht, K. T. et al. Mol. Pharmacol. 47:1028–1034 (1995)).

Endotoxin (lipopolysaccharide or LPS) is a major constituent of the outer cell membrane of Gram negative bacteria. There exists two major sources for introduction of endotoxin into the body; through infection by Gram negative bacteria and by translocation from the digestive system.

Because endotoxin is often released from Gram negative bacteria, its presence is often closely monitored by the human immune system as a signal of bacterial infection. In blood, monocytes, macrophages and neutrophils respond to the presence of endotoxin by releasing a cascade of cytokines such as tumor-necrosis factor, interleukin-1, interleukin-6 and interleukin-8 and other biological mediators such as nitric oxide as well as an array of secondary mediators (e.g., prostaglandins, leukotrienes, interferons, platelet-activating factor, endorphins and colony-stimulating factors). These cytokines and inflammatory mediators are used to signal other cells to mount an immune attack on the invading organism. When endotoxin levels exceed the ability of the immune system to control the perceived infection, the immune system can over respond and produce pathophysiological concentrations of these cytokines and inflammatory mediators which influence vasomotor tone, rmicrovascular permeability and the aggregation of leukocytes and platelets causing a syndrome termed systemic inflammatory response syndrome (or SIRS). This syndrome can ultimately result in septic hypotensive shock, disseminated intravascular coagulation, multiorgan failure and possibly death (Bone, R. C. Clinical Microbiology Rev. 6:57–68, (1993), Bone, R. C. Chest 100: 802–808 (1991)).

Besides bacterial infection, the digestive system is another ever-present source of endotoxin. Gram negative bacteria are present at very high concentration in the digestive tract or gut. The enormous nutrient-absorbing surface area of the digestive system provides an ideal opportunity for endotoxin to translocate from the gut to the blood supply. However, in the healthy gut, this translocation event appears to be relatively rare, and the small amount of endotoxin that is routinely taken up is rapidly cleared by the liver. In fact, non septic endotoxemia is believed to be a manifestation of impaired Kupffer cell function (Lahnborg, G. et al. Scand J. Gastroent. 16, 481–489 (1981), (Ueno, M, et al., Cells of the Hepatic Sinusoid vol. 2; 293–296 (1989), Kupffer cell Foundation, P.O. Box 5815, 2280 HV Rijswijk, The Netherlands Editors E. Wisse, D. L. Knook, K. Decker.

As described above, under normal physiological conditions, recognition of endotoxin at very low levels leads to an inflammatory response that can assist in destruction of the infectious agent. In contrast to this normal physiological response to endotoxin, pathological conditions may be found where exposure to even lov levels of endotoxin can lead to extreme responses and result in injury. These conditions are observed after endotoxin-sensitive cells are exposed to agents that further enhance their susceptibility to endotoxin. Experimentally, this phenomenon, known as "priming", can be readily seen in animal models during infection with Gram positive agents (*Bacillus calmette*, Guerin strain (BCG); Vogel, S. N., el al., J. Immunol, 124: 2004–9. (1980)) exposure to galactosamine (Galanos, C. el al., Proc. Natl. Acad. Sci. 76: 5939–5943 (1979) Shiratori, Y et al. Cells of the Hepatic Sinusoid pp. 313–318 (1989), Iwaki, Y. el al. ibid. pp. 351–352) or by treatment with interferon gamma (Rose et al., Inf and Immun. 63 833–839 (1995)). Once priming has occurred, a hyper-immune response can be triggered by a small amount of endotoxin, regardless of its source.

Normal liver contains two groups of cells: parenchymal cells that make up the bulk of the liver and are responsible for major metabolic functions (e.g. gluconeogenesis, bile formation, urea synthesis), and nonparenchymal cells that are less well characterized. Kupffer cells, one type of nonparechymal cell, are resident macrophages of the liver and comprise the greatest population of macrophages in the body. These cells play an important role in host defense mechanisms by phagocytizing blood-borne particles such as foreign bodies and bacteria (Saba, T. M. Arch Intern Med. 126, 1031–1052. (1970)).

Kupffer cells also, by virtue of their predominance in the periportal area, remove toxic bacterial products including endotoxin absorbed from the gut via splanchnic circulation (Freudenberg, M. A. et al. British J. of Exp. Path. 63: 56–64 (1982), Mathison, JC & Ulevich, R. J. J. Immunol. 123:2133–2143 (1979), Ruiter el al. Lab Invest. 45; 38–45, (1981), Van Bossuyt, H. and Wisse, E. Cell. Tiss Res. 251: 205–215 (1988), Van Bossuyt, H. and Wisse, J. Hepatol., 7: 45–56 (1988)). Removal of endotoxin by these cells is a critical function, as increased levels in the blood can ultimately lead to systemic inflammatory response syndrome.

Alcohol has been reported to affect Kupffer cell functions such as phagocytosis, bactericidal activity and cytokine production (Martinez, F. et al. Alcohol 9: 455–458. (1992), Yamada et al. Liver 11, 220–224. (1991)). Additionally, serum endotoxin levels are increased in alcoholics (Fuklui, H. el al. Hepatology 12: 162–169 (1991)), and increased serum TNF in alcoholic patients has been reported by Stahnke et al. (Stahnke L. L., et al. Cells of the Hepatic Sinusoid. Leiden, The Netherlands: Kupffer Cell Foundation, pp. 472–475 (1991), Felver el al. Alcohol Clin Exp Res 14: 255–259 (1990)). This latter observation is consistent with the idea that Kupffer cells of patients with alcoholic liver disease are activated (ie. producing cytokines). Nanji el al. showed that plasma endotoxin levels increased in rats on the Tsukamoto-French protocol and that levels correlated well with pathology scores (Nanji, A. A. el al. Aer. J. Pathol. 142: 367–373 (1993)). Accordingly, it is hypothesized that endotoxin derived from intestinal bacteria is a causative factor in alcohol-induced liver injury and that activation of Kupffer cells by endotoxin is involved in the mechanism of liver pathophysiology. In support of this theory), one study has shown that administration of ethanol leads to less hepatic damage when accompanied by prior antibiotic decontamination of the gut (Adachi, Y. et al. Gastroenterology 108:218–224 (1995)). Thus, bacterial components that are absorbed from the gut may play a role in alcohol-induced liver injury.

The mechanism of induction of alcoholic liver disease by alcohol and endotoxin is not entirely clear. In the normal physiological state, endotoxin removal by Kupffer cells is done without activating the cell (inducing cytokines) as is typically seen in other endotoxin-sensitive cells. Presumably this lack of response is due to a "desensitization" (Hafenrichter, D. G. et al., Shock 2: 251–256 (1991)) combined with a low permeability of the gut to endotoxin, which keeps endotoxin levels too low to stimulate a cytotoxic response. It is possible that the toxicity of alcohol may be related to its propensity to increase the permeability of the gut lining to endotoxin. Response of Kupffer cells to this increased level of endotoxin would trigger two events: an increase in endotoxin uptake, and an inflammatory reaction.

Once endotoxin concentrations rise to perceived threshold pathological levels, Kupffer cells can respond like other macrophage cells and synthesize cytokines similar to those secreted by circulating macrophages (Thurman, R. G. et al. pp. 185–203, Falk symposium 78 (Proceedings of the 78th Falk symposium) Gerok, W., Decker, K., Andus, T., and Gross, V. eds. Kluwer Academic Publishers, Boston. (1995), Decker, K. et al. Cells of the Hepatic Sinusoid pp. 171–175 (1989), Karck et al. ibid. pp. 210–211). Kupffer cells of septic rats induced by cecal ligation and of endotoxin-treated rats release large quantities of tumor necrosis factor (TNF), interleukin-1 (IL-1) and superoxide that damage hepatocytes (Monden, K. et al. Res Exp Med (Berl), 191: 177–187. (1991), Monden, K., et al. J Surg Res, 50: 72–76. (1991)). These cytokines and cellular mediators participate in inflammation, immune responses, and modulation of hepatocyte metabolism (Nolan, J. P. Hepatology, 1: 458–65. (1981)). These mediators produced by activated Kupffer cells participate in several diseases including hepatic injury seen in sepsis (Monden el al. Res Exp Med (Berl), 191: 177–187. (1991), Monden, K. et al. J Surg Res, 50: 72–76. (1991)), obstructive jaundice (Adachi et al. J Hepatol, 16: 171–176. (1992)), and transplantation ((Marzi el al., Transplant Proc, 22, 2004–2005 (1990)). In the liver, these cytokines cause toxic reactions such as cellular ballooning or blebbing, and necrosis (Wisse, E., et al., Cells of the Hepatic Sinusoid vol. 2; 1–8 1989 Kupffer cell Foundation, P.O. Box 5815, 2280 HV Rijswijk, The Netherlands Editors E. Wisse, D. L. Knook, K. Decker).

Kupffer cells can be induced to be highly sensitive to endotoxin, and to respond vigorously to its presence. Kupffer cells can be hypersensitized to the presence of endotoxin by disease, infection or hepatotoxicants (Laskin, D. L. Cells of the Hepatic Sinusoid pp. 294–287 (1989), Vogel, S. N., et al., J. Immunol, 124: 2004–9. (1980), Galanos, C. et al., Proc. Natl. Acad. Sci. 76: 5939–5943 (1979), Shiratori, Y. et al. Cells of the Hepatic Sinusoid pp. 313–318 (1989), Iwaki, Y. et al. ibid. pp. 351–352).

Experimentally, chronic administration of alcohol leads to an adaptive increase in ethanol metabolism involving alcohol dehydrogenase (Hawkins, R. & Khanna, J. M., Can. J. Physiol. Pharmacol. 44:241–257 (1966), Mendelson, J. H. & Mello, N. K. Ann N Y Acad Sci, 133: 828–845. (1966), DeCarli, L. M. & Lieber, C. S. J Nutr, 91: 331–336. (1967), Porta, B. A. & Gomez-Dumm, C. L. Lab Invest, 18: 352–364. (1968), Tobon, F. & Mezey, E. J. Lab Clin Med, 77: 110–121. (1971), Thurman el al., Molecular Pharmacol. 12: 156–166 (1975)). One consequence of this hyper metabolic state due to alcohol metabolism may be hypoxia in the liver. As seen in injury due to ischemia/reperfusion of other organs, a typical response to this hypoxia would be generation of cytokines and other cellular mediators which would trigger further inflammation, and a positive feedback loop of immune responses and compromisation of hepatic metabolism (Nolan, J. P., Hepatology 1: 458–465 (1981)).

The present inventors concluded that therapeutic intervention towards blocking this swift increase in alcohol metabolism by suppressing inflammatory responses by the Kupffer cells may enable the liver to exit the positive feedback cycle of generation of inflammatory molecules and degradation of liver function, and allow recovery from the disease state. In animal models, selective inactivation of Kupffer cells by treatment with gadolinium chloride prevented alcoholic injury such as fatty changes, inflammation and necrosis, suggesting that Kupffer cells participate in the early phases of the disease process (Adachi, Y. et. al. Hepatol. 20: 453–460 (1994)). However, destruction of Kupffer cells in human subjects is not practical as these are important immune system cells serving vital functions in the liver. The inventors thus undertook to prevent activation of Kupffer cells by endotoxin, without destruction of the cells themselves.

Research directed to inactivation of Kupffer cells has now led to the surprising and unexpected discovery that the inflammatory response triggered by endotoxin (in the presence or absence) of alcohol can be blocked by the compounds described in this invention. This antagonism of endotoxin activity can be assessed in the liver in several ways including in vitro analysis of blocking intracellular signaling induced by endotoxin in isolated Kupffer cells and in vivo analysis of blocking the swift increase in metabolism triggered by alcohol and endotoxin. The compounds of the invention were designed to be analogs of the bacterial lipopolysaccharide molecule which act as endotoxin antagonists.

The bacterial lipopolysaccharide (LPS) molecule, a component of endotoxin, has three main regions: a long chain polysaccharide (O Antigen), a core region, and a Lipid A region. The entire lipopolysaccharide molecule, as well as some of its individual components, possess the toxic effects described above. Most of these toxic effects, however, are believed to be attributable to the Lipid A portion of the molecule. Structurally, Lipid A from *E. coli*, shown below, is composed of a disaccharide acylated by long chain fatty acids.

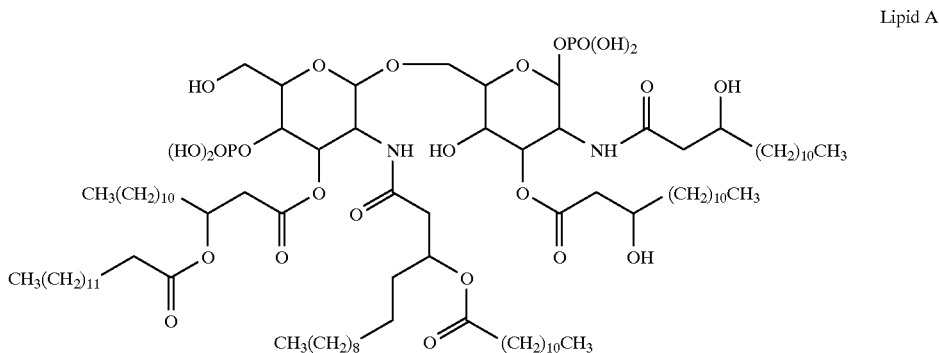

Lipid A

SUMMARY OF THE INVENTION

The invention concerns the use of novel Lipid A analogs, which function as Lipid A antagonists, for the treatment of alcoholic liver disease. Specifically, the method of the invention involves administration of novel Lipid A analogs to mammals suffering from alcoholic liver disease to arrest or reverse the progression of the disease.

The compounds of the invention typically have a generic structure comprising a diglucosamine disaccharide substituted with alkyl or acyl groups, wherein the term alkyl refers to organic groups which may be straight or branched, saturated or unsaturated, and which may be optionally substituted with one or more amino, carbonyl, ether, hydroxy or alkoxy groups or halogen atoms at any position along the aliphatic group.

DETAILED DESCRIPTION OF THE INVENTION

Definitions

Figure 1:
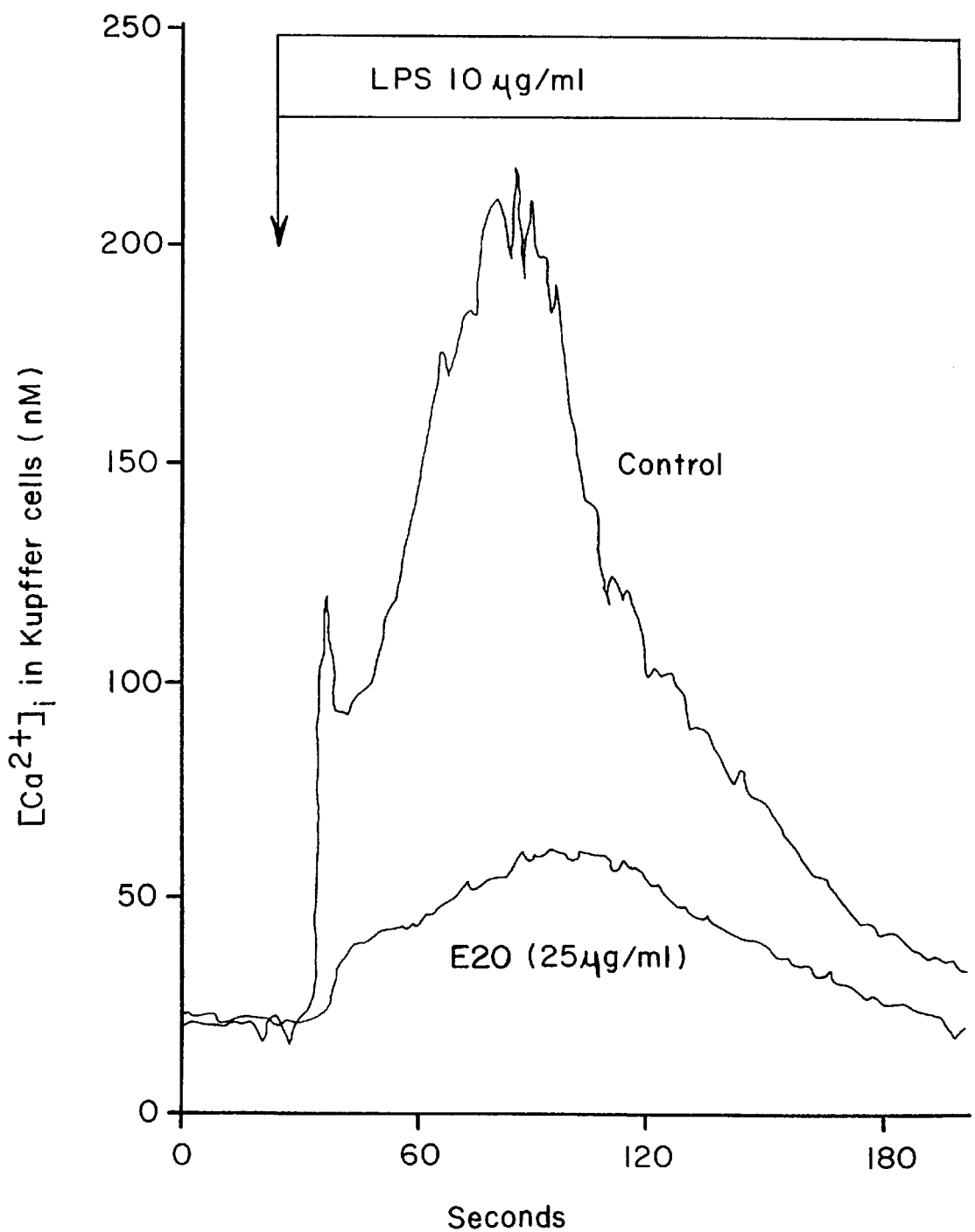
FIG. 1 shows the increase in $Ca^{2+}$ in an isolated Kupffer cells caused by endotoxin over time.

In accordance with the present invention and as used herein, the following terms are defined:

The term "lipid A analogs" refers to chemically synthesized analogs of naturally occurring lipid A comprising diglucosamine disaccharides substituted with acyl or alkyl groups. The term "alkyl" refers to aliphatic organic groups which may be branched or straight, saturated or unsaturated and which may be optionally substituted with one or more amino, carbonyl, ether, hydroxy or alkoxy groups or halogen atoms at any position along the aliphatic group.

The term parenteral as used herein includes subcutaneous, intravenous, intramuscular, and intraarterial injections with a variety of infusion techniques. Intraarterial and intravenous injection as used herein includes administration through catheters. The term "prodrug" as used herein refers to any compound that has less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, phosphates and urethanes, included herein as examples. The groups illustrated are exemplary, not exhaustive and one skilled in the art could prepare other known varieties of prodrugs. Such prodrugs of the compounds of Formula 1 fall within the scope of the present invention.

The term "pharmaceutically acceptable salt" includes salts of compounds of Formula 1 derived from the combination of a compound of this invention and an organic or inorganic acid or base. The compounds of Formula 1, for example, are useful in both non-ionized and salt form. In practice the use of salt form amounts to use of base form; both forms are within the scope of the invention.

The term "geometric isomers" refers to "trans" or "cis" (or "entgegen" or zusammen") isomers as generally understood by those skilled in the art. All geometric isomers are within the scope of the invention.

Further, compounds of the present invention may contain asymmetric carbon and sulfur atoms and hence can exist as stereoisomers, both enantiomers and diastereomers. All stereoisomers and mixtures thereof are considered to fall within the scope of the present invention. The synthetic examples cited herein provide the most preferred isomers. It is evident that in addition to the sugar moiety, additional asymmetric carbons may be present in compounds of Formula 1, for example being present in the side chains. In this event, all of the resulting diastereomers are considered to fall within the scope of the present invention.

LPS Antagonists

One aspect of the present invention relates to a method of treating alcoholic liver disease comprising administration to an individual in need of such treatment a compound comprising a Lipid A analog which functions to antagonize the effects of naturally occurring Lipid A.

Another aspect of the present invention relates to the novel use of substituted liposaccharides which comprise compounds of the general Formula 1

Formula 1

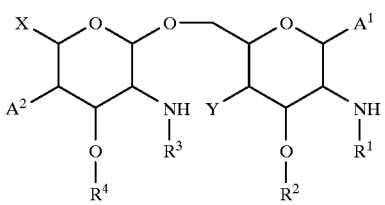

wherein $A^1$ and $A^2$ are hydroxyl, carboxyl, or oxidized phosphorous groups, and X is hydrogen, alkoxy, alkyl, alkoxy-alkyl, methoxyalkyl, phosphoryl, phosphoryl-alkyl, alkenyl, polyhydroxyalkyl, and protected forms therof, preferably having 1–15 carbon atoms, $R^1$ through $R^4$ are aliphatic organic groups which may be branched or straight-chained, saturated or unsaturated and which may comprise or be optionally substituted with one or more amino, carbonyl, ether, hydroxy, phosphate, or alkoxy groups or halogen atoms at any position along the aliphatic group. Preferably, at least one, and more preferably two of the R groups are ether moeities.

Specific embodiments of the invention relate to the novel use of compounds of the general Formula 1 where at least one of $R^1$, $R^2$, $R^3$, or $R^4$ is:

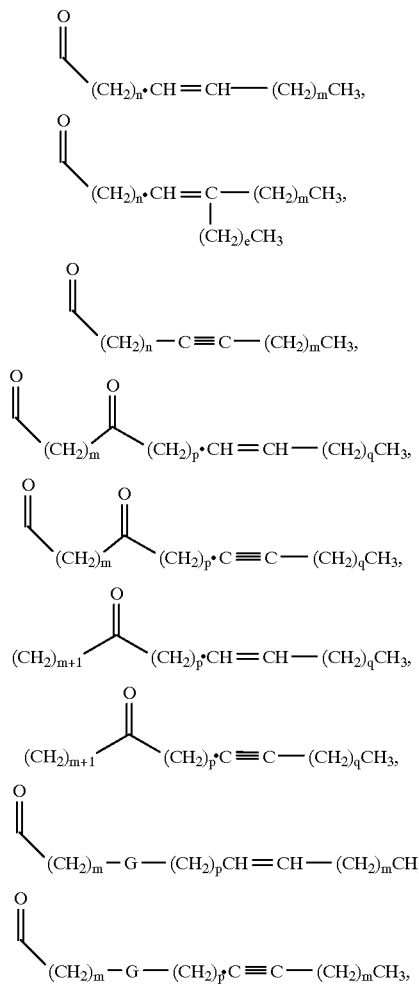

-continued

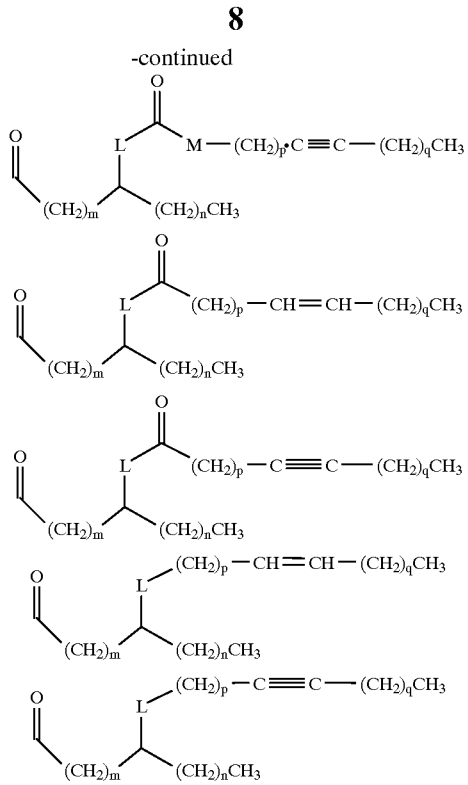

wherein each L is O, N or C; each M is O or N; each e, independently, is an integer between 0 and 14 inclusive; each G, independently, is N, S, SO or $SO_2$; each m, independently, is an integer between 0 and 14 inclusive; each n, independently, is an integer between 0 and 14; each p, independently, is an integer between 0 and 10, inclusive; and each q, independently, is an integer between 0 and 10 inclusive; each of the remaining $R^1$, $R^2$, $R^3$, and $R^4$, independently, is:

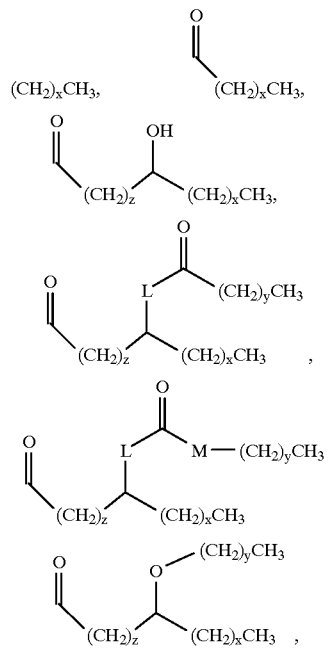

-continued

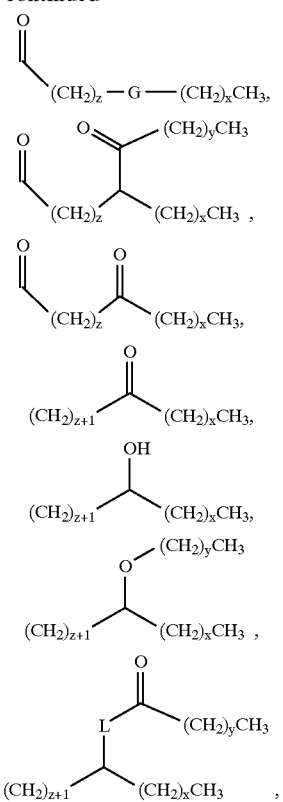

or

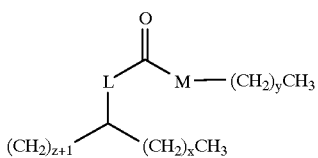

wherein each L is O, N, or C; each M is 0 or N; each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

$A^1$ and $A^2$, independently, are selected from the group consisting of

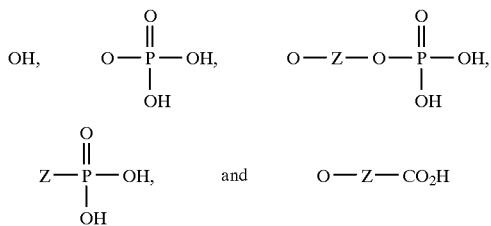

where Z is straight or branched C1 to C10 alkyl; X is selected from the group consisting of hydrogen, J', —J'—OH, —J'—O—K',—J'—O—K'—OH, and —J'—O—PO$(OH)_2$ where each J' and K', independently, is straight or branched C1 to C5 alkyl; Y is selected from the group consisting of hydrogen, hydroxy, halogen,, lower alkoxy and lower acyloxy and pharmaceutically acceptable salts thereof.

Preferred are compounds where at least one of $R^1$, $R^2$, $R^3$, or $R^4$ is:

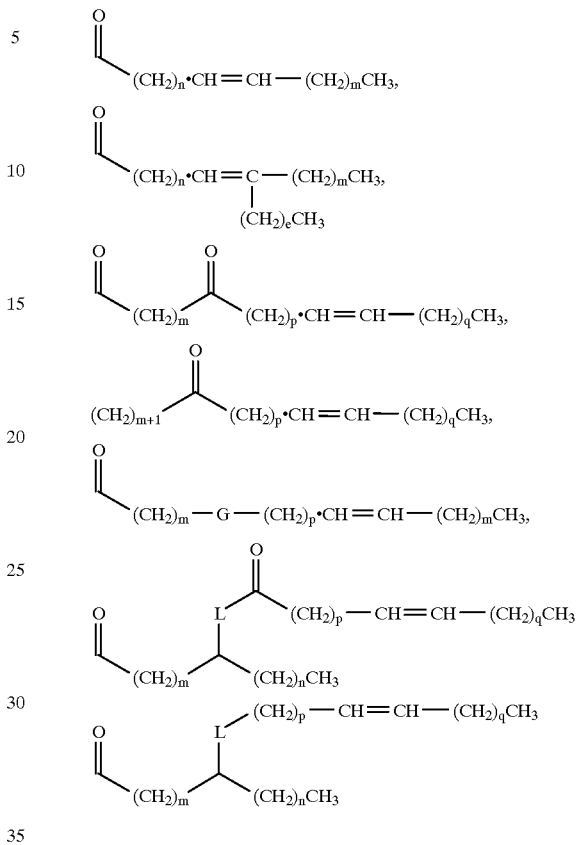

wherein each L is O, N or C; each e, independently, is an integer between 0 and 14 inclusive; each G, independently, is N, S, SO or $SO_2$; each m, independently, is an integer between 0 and 14 inclusive;, cacti n, independently, is an integer between 0 and 14; each p, independently, is an integer between 0 and 10, inclusive; and each q, independently, is an integer between 0 and 10 inclusive; each of the remaining $R^1$, $R^2$, $R^3$ and $R^4$, independently, is:

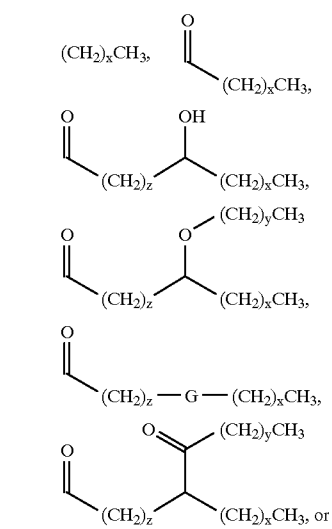

-continued

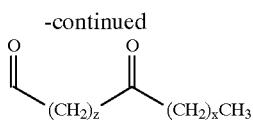

wherein each x, independently, is an integer between 0 and 14 inclusive; each y, independently, is an integer between 0 and 14 inclusive; each z, independently, is an integer between 0 and 10 inclusive; and each G, independently, is N, O, S, SO, or $SO_2$;

$A^1$ and $A^2$, independently, are selected from the group consisting of

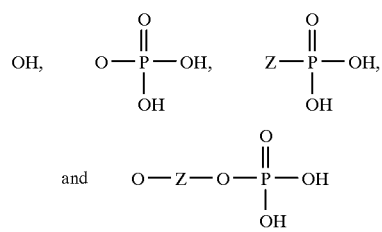

where Z is straight or branched C1 to C10 alkyl; X is selected from the group consisting of —J'—OH, —J'—O—K', —J'—O—K'—OH, and —J'—O—PO(OH)$_2$ where each J' and K', independently, is straight or branched C1 to C5 alkyl; Y is selected from the group consisting of hydroxy, halogen, lower alkoxy and lower acyloxy; and pharmaceutically acceptable salts thereof.

The most preferred compounds are those compounds of Formula 1 where at least one $R^1$, $R^2$, $R^3$, or $R^4$ is:

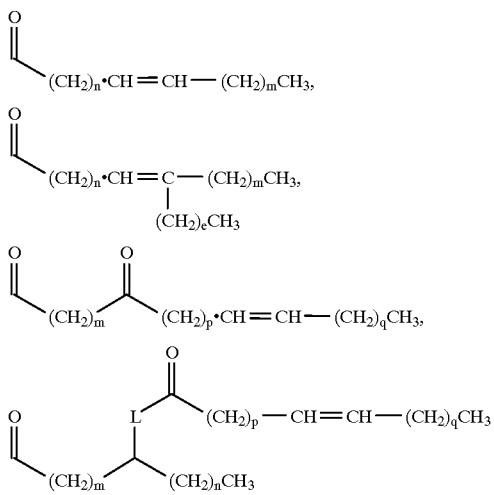

wherein L is O, N or C; each C, independently, is an integer between 0 and 14 inclusive; each in, independently, is an integer between 0 and 14 inclusive; each n, independently, is an integer between 0 and 14; each p, independently, is an integer between 0 and 10, inclusive; and each q, independently, is an integer between 0 and 10 inclusive, each of the remaining $R^1$, $R^2$, $R^3$, and $R^4$, independently, is:

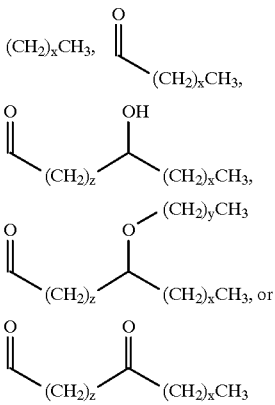

wherein each x, independently, is an integer between 0 and 14 inclusive; each y, independently, is an integer between 0 and 14 inclusive; each z, independently, is an integer between 0 and 10 inclusive, $A^1$ and $A^2$ are

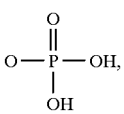

X is —J'—OH or —J'—O—K', where each J' and K' is, independently, straight or branched C1 to C5 alkyl; Y is selected from the group consisting of hydroxy and lower acyloxy; and pharmaceutically acceptable salts thereof and pharmaceutically acceptable salts thereof.

General Synthetic Methods

The invention is also directed to processes for preparing the compounds of generic Formula 1. Disclosed herein are general synthetic routes for preparing variously substituted compounds of this invention. The synthesis of exemplary compounds of this invention, compounds E1 and E21, are shown below in Examples 1 and 2.

Most of the reagents and starting materials are well known to those skilled in the art. Certain reagents and starting materials for this preparation are described in detail by Christ, et al. in U.S. Pat. No. 5,530,113, which is hereby incorporated by reference.

Although the schemes in the Examples below describe the preparation of compounds E1 and E21, use of alternate starting materials well known to those of ordinary skill in the art will yield other compounds of Formula 1. Thus the one of ordinary skill in the art would be able to derive from the schemes below, methods for the synthesis of other compounds of the invention without undue experimentation. For example, use of alternative alkylating agents in the preparation of intermediate U of Example 1 will provide analogs with structurally differing substituents at $R^1$ (Example 1). Similarly, the substitution pattern at $R^2$ can be controlled by the use of the proper alkylating agent in the preparation of intermediate O. Further, substitution of suitable alternative compounds for intermediate E in the preparation of intermediate G will produce analogs which differ with respect to $R^3$. The syntheses of many of the side chains of the invention are provided in Christ et al., U.S. Pat. No. 5,530,113 and EP 92309057.5, which are both incorporated by reference in their entirety.

Thus the syntheses in Examples 1 and 2 below provide versatile pathways to compounds E1 and E21 of this invention and related analogs. Procedures for the preparation of other compounds of the invention are also described in U.S. patent application Ser. No. 07/935,050, now U.S. Pat. No. 5,530,113, and U.S. patent application Ser. No. 08/461,675, now U.S. Pat. No. 5,750,664, the disclosures of which are herein incorporated by reference.

EXAMPLES

The compounds of this invention and their use can be understood further by the following examples which illustrate some of the methods by which these compounds are made and used. These examples should not be construed as specifically limiting the invention and variations of the invention, now known or later developed, are considered to fall within the scope of the present invention as claimed.

Unless otherwise noted, all reactions were conducted under an inert atmosphere. Intermediates and final products gave spectral analysis (for example, nuclear magnetic resonance spectroscopy and/or mass spectroscopy) consistent with their proposed structures. Reactions were monitored by silica gel thin layer chromatography. Preparative chromatography, unless otherwise noted, was performed on silica gel.

Example 1

Synthesis of Compound E1

A representative synthesis of the $R^4$ side chain of compound E1 is outlined below. The preparation of variations of this side chain may be achieved by replacing the starting material with other suitable starting materials. For example, the length of branching of this side chain may be varied by starting with the appropriately structured starting material.

A representative preparation of the "left" portion of the molecule is outlined below:

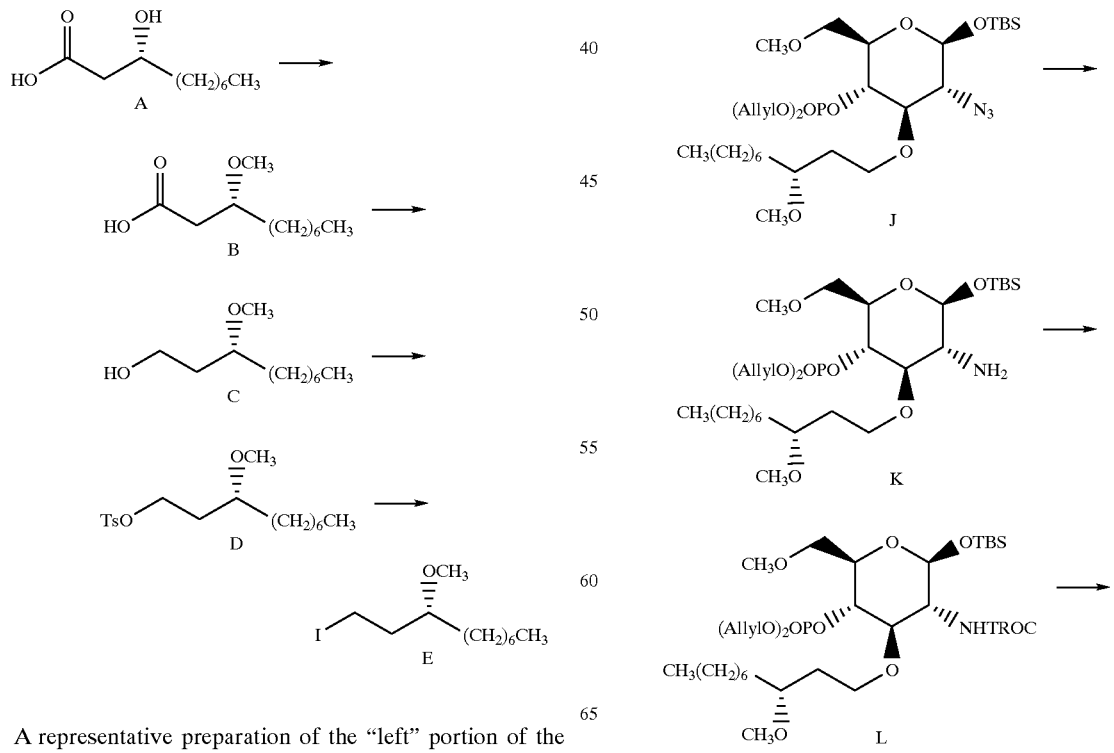

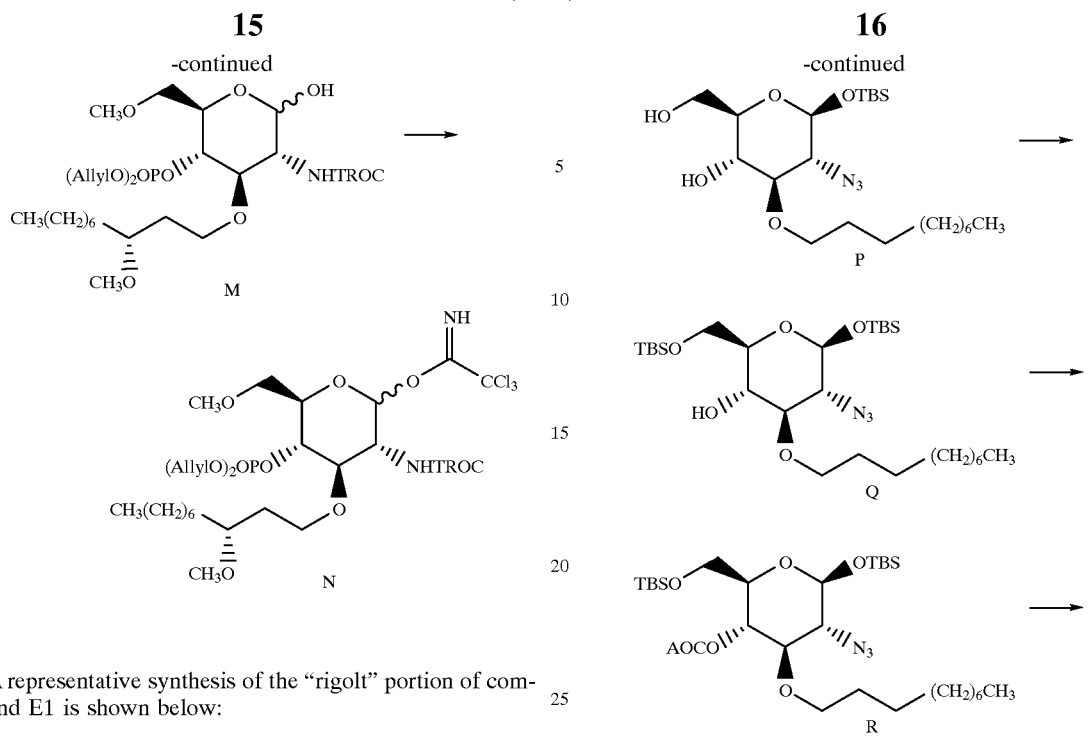
A representative synthesis of the "rigolt" portion of compound E1 is shown below:
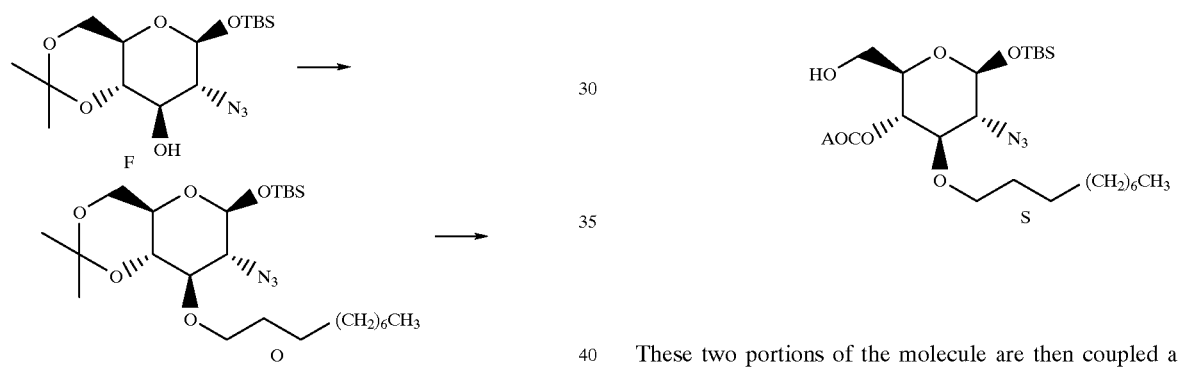
These two portions of the molecule are then coupled as outlined below and further elaborated to give compound E1.
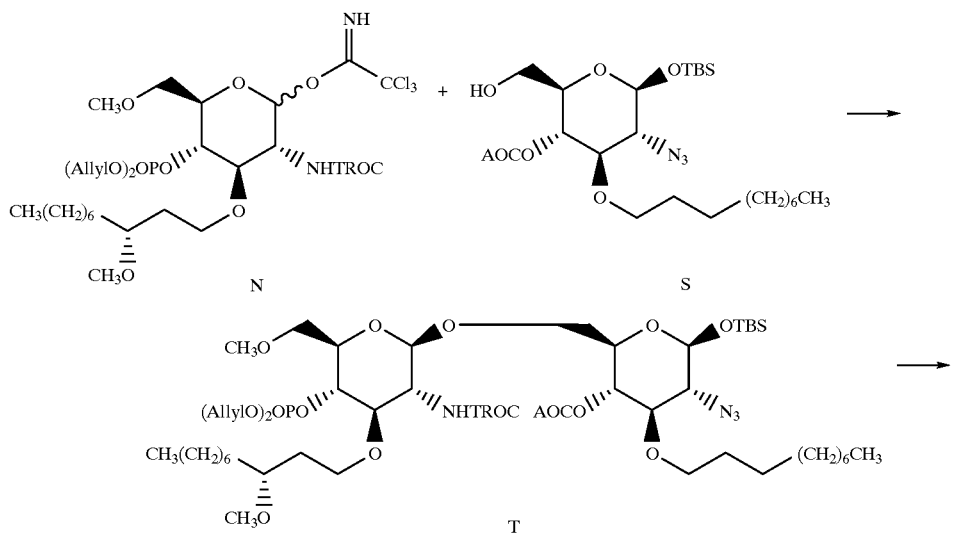

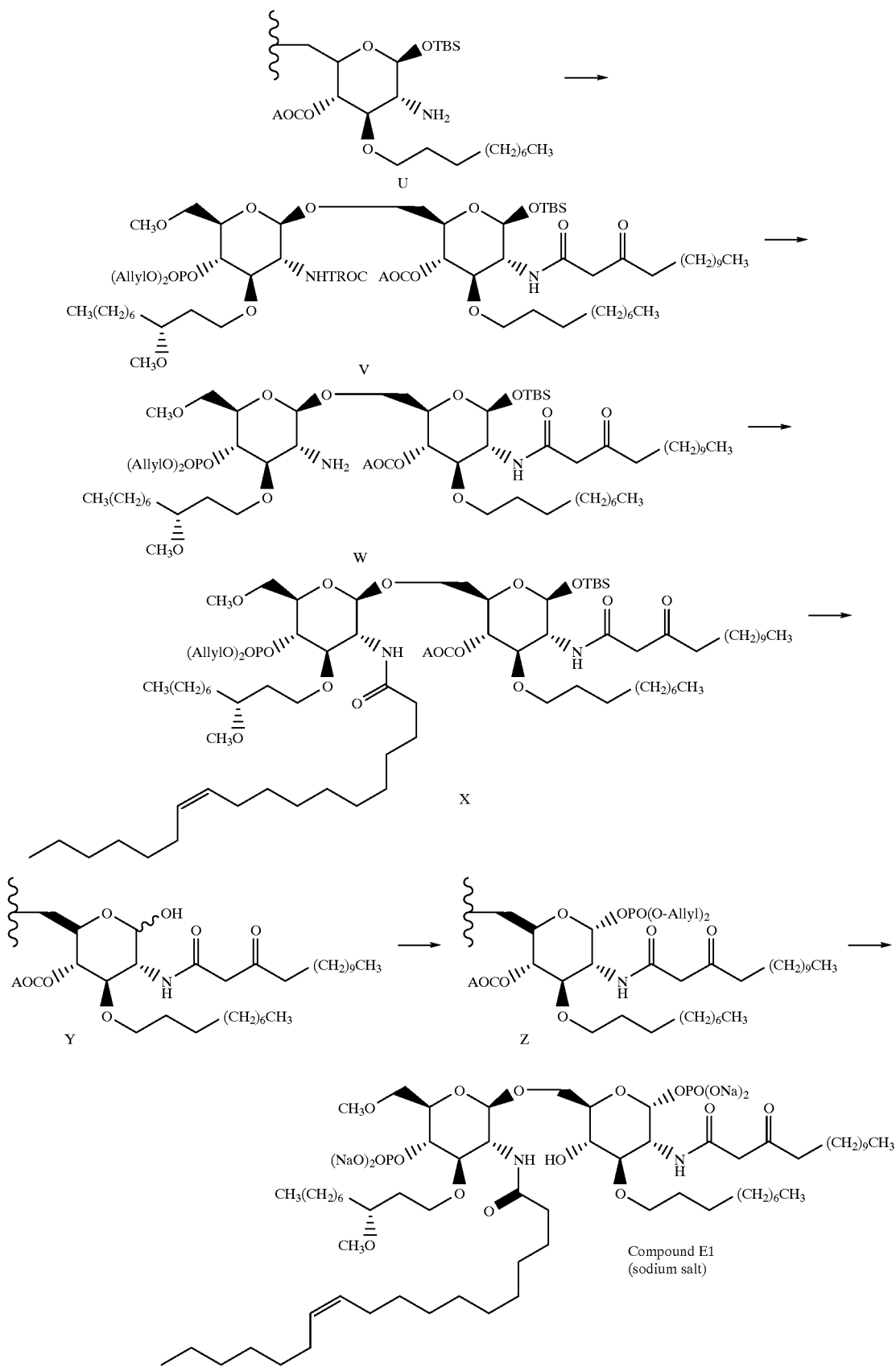

The following is a detailed description of the synthetic scheme outlined above.

Intermediate B

To a suspension of intermediate A (15 g), prepared by the method of Christ, et al., U.S. Pat. No. 5,530,113 and European patent application 92309057.5 (see scheme above), in $CH_2Cl_2$ (150 ml) and 48% $HBF_4$ (29.2 g), cooled via ice-bath, was added $TMSCHN_2$ (165 ml as a 2 M solution in hexane). The mixture was stirred until the reaction was almost complete by TLC and then methanol (20 ml) was added followed by acetic acid (10 ml).

Aqueous sodium bicarbonate was added and the mixture extracted with methylene chloride. The mixture was dried (sodium sulfate) and the solvent removed under reduced pressure. Chromatography of the residue gave B, 14.9 g.

Intermediate C

To a cold (0° C.) solution of B (14.9 g) in methylene chloride (100 ml) was slowly added diisobutylaluminum hydride (140 ml as a 1 M solution in hexanes) until reaction was complete as determined by TLC. The reaction was quenched by the addition of aqueous 1 N hydrochloric acid (100 ml) followed by conc. hydrochloric acid (50 ml). The layers were allowed to separate and the aqueous layer was re-extracted with $CH_2Cl_2$. The combined organic layers were then washed with brine, dried over sodium sulfate and concentrated under reduced pressure. After purification by silica chromatography, 12.06 g of intermediate C was obtained.

Intermediate D

To a solution of C (10.64 g) in methylene chloride (40 ml) was added triethylamine (15.75 ml), p-toluenesulfonyl chloride (11.86 g) and dimethylaminopyridine (690 mg). The resulting suspension was allowed to stir until reaction was complete as determined by TLC then quenched via water work-up with methylene chloride extraction. After purification by silica chromatography, 18.7 g of D was obtained.

Intermediate E

To a solution of D (18.7 g) in 200 ml of acetone was added sodium iodide (24.6 g). The mixture heated at reflux for 1.5 hours, the solvent removed under reduced pressure and the residue partitioned between water and hexane. The organic layer was separated, dried (sodium sulfate) and the solvent removed C (silica) gave 15.4 g of E as a colorless liquid.

Intermediate F

This compound was prepared by the method of Christ, et al., described in U.S. Pat. No. 5,530,113 and European Patent Application 92309057.5.

Intermediate G

To a solution of 18.6 g of intermediate F and 15.4 g of intermediate E in hexane was added 23.9 g of silver oxide and the mixture refluxed overnight. The mixture was cooled, filtered through diatomaceous earth, the solvent removed and the residue chromatographed (silica) to give intermediate G (21 g) as a colorless syrup.

Intermediate H

To a cold (0° C.) solution of intermediate G (21 g) in methylene chloride was added dropwise 3.5 ml of 48% tetrafluoroboric acid. After 5 minutes the mixture was washed with aqueous sodium bicarbonate solution and with brine. The mixture was concentrated under reduced pressure and chromatographed (silica) to give intermediate H, 18.7 g, as a colorless syrup.

Intermediate I

To a solution of intermediate H (17.6 g) in neat methyl iodide (105 ml) was added silver oxide (83 g). The mixture was stirred overnight and then diluted with hexane and filtered through diatomaceous earth. The mixture was concentrated under reduced pressure and the residue dissolved in methylene chloride (40 ml). The mixture was cooled to 0° C. and to it was added imidazole (2.44 g) and t-butyldimethylsilyl chloride (4.7 ml). It was stirred overnight and 150 ml of sodium bicarbonate solution was added. The organic layer was dried (sodium sulfate) and chromatographed (silica) to give intermediate I, 10.5 g, as a colorless syrup.

Intermediate J

Intermediate I was dissolved in 100 ml of methylene chloride to which was added diallyldiisopropylphosphoramidite (7.4 ml), followed by tetrazole (6.37 g). The mixture was cooled and stirred for 20 minutes. A suspension of meta-chloroperoxybenzoic acid (24.2 mmol) in 50 ml of methylene chloride was added over 15 minutes while the temperature of the reaction was maintained below −60° C. Sodium bicarbonate solution was added and the organic layer separated, dried (sodium sulfate) and the solvent removed under reduced pressure. Chromatography (silica) gave 14 g of a colorless syrup of intermediate J.

Intermediate K

To a suspension of 39.5 g of di(thiophenyl)tin (prepared by the method of Christ, et al., European patent application 92309057.5) in 235 ml of methylene chloride was added thiophenol (12 ml). To this mixture was added triethylamine dropwise over 15 minutes. A portion (150 ml) of this "tin reagent" mixture was added dropwise over 15 minutes to a solution of intermediate J (12.9 g) in 25 ml of methylene chloride. The remainder of the "tin reagent" was added over 30 minutes to drive the reaction to completion. The mixture was diluted with ethyl acetate and washed with aqueous 1 N sodium hydroxide and with brine. The organic layer was dried (sodium sulfate), the solvent removed and the residue chromatographed to give 11.1 g of a yellow syrup, intermediate K.

Intermediate L

To a cold solution of intermediate K (11.1 g) and pyridine (7.1 ml) in 80 ml of methylene chloride was added trichloroethyl chloroformate (2.9 ml) and the mixture was stirred overnight. Aqueous sodium bicarbonate solution was added, the organic layer was separated, dried (sodium sulfate) and the solvent removed under reduced pressure. Chromatography gave intermediate L, 12.96 g as a light yellow solid.

Intermediate M

Intermediate L, 12.96 g, was dissolved in methylene chloride. To this mixture was added a 6 M solution of hydrogen fluoride in acetonitrile and the mixture stirred for 4 hours. Aqueous sodium bicarbonate solution was added, the organic layer was separated, dried (sodium sulfate) and the solvent removed under reduced pressure. Chromatography gave 10.9 g of an amber syrup, intermediate M.

Intermediate N

To a solution of intermediate M (9.5 g) in 50 ml of trichlororacetonitrile was added potassium carbonate (15 g) and the mixture stirred for 10 minutes. The mixture was filtered through diatomaceous earth and the solvent removed under reduced pressure. Chromatography gave 14.5 g, intermediate N.

Intermediate O

To a solution of intermediate F (160 g) in hexane (475 ml) and iododecane (474 ml) was added silver oxide (723 g). The mixture was heated at 70° C. in the dark for 2 hours and filtered through diatomaceous earth. The solution was concentrated under reduced pressure and the residue chromatographed to give 221 g of intermediate O as a colorless oil.

Intermediate P

To a solution of intermediate O (30 g) in methylene chloride (90 ml) and acetonitrile (90 ml) was added a solution of 48% aqueous hydrogen fluoride (9 ml) in acetonitrile (81 ml). The mixture was stirred for 30 minutes and 350 ml of aqueous sodium bicarbonate was added. The mixture was extracted with methylene chloride. The organic layer was dried (sodium sulfate), the solvent removed under reduced pressure and the residue chromatographed to yield 30 g of intermediate P as a yellow oil.

Intermediate Q

To a cold (0° C.) solution of intermediate P (30 g) and imidazole (10.2 g) in methylene chloride (500 ml) was added t-butyldimethylsilyl chloride (10.85 g). The mixture was stirred for 1½ hours and then poured onto 400 ml of saturated aqueous ammonium chloride. The organic layer was separated, dried (sodium sulfate). the solvent removed under reduced pressure and the residue chromatographed to give 34.5 g of intermediate Q as a colorless syrup.

Intermediate R

To a cold (0° C.) solution of intermediate Q (32.2 g) and pyridine (184. ml) in toluene (213 ml) was added a 1.94 M solution of phosgene in toluene. After 20 minutes, allyl alcohol (31 ml) was added and the mixture stirred for 30 minutes. Aqueous sodium bicarbonate was added, the organic layer separated, dried (sodium sulfate) and the solvent removed under reduced pressure. Chromatography gave 36.9 g of intermediate R as a colorless syrup.

Intermediate S

To a solution of 2.4 ml of 48% aqueous hydrogen fluoride in 48 ml of acetonitrile was added a solution of intermediate R (20 g) in methylene chloride (24 ml) and the mixture stirred overnight. Aqueous sodium bicarbonate solution was added, the organic layer separated and dried (sodium sulfate) and the solvent removed under reduced pressure. Chromatography yielded 11 g of intermediate S as a colorless syrup.

Intermediate T

Intermediate S (8.97 g) and intermediate N (14.5 g) were dissolved in toluene (20 ml) and the mixture dried by azeotropic removal of the solvent. This procedure was repeated three times. The dried mixture was dissolved in 50 ml of methylene chloride which was slowly added to a solution of silver triflate (5.8 g) in 50 ml of methylene chloride. The mixture was stirred for 10 minutes and 250 ml of aqueous sodium bicarbonate solution and 250 ml of 10% aqueous sodium thiosulfate was added. The organic layer was separated, dried (sodium sulfate) and the solvent removed under reduced pressure. Chromatography gave 13 g of intermediate T as a pale yellow syrup.

Intermediate U

To a solution of intermediate T in methylene chloride (10 ml) was slowly added tin(II)tris-benzenethiolate triethylamine complex (12 ml of a 0.5 M solution in methylene chloride). After 10 minutes, an additional equivalent of tin reagent was added. After an additional 15 minutes, an additional equivalent was added. After 15 minutes ethyl acetate (250 ml) was added and the mixture extracted with 1 N aqueous sodium hydroxide solution (250 ml). The mixture was dried (sodium sulfate) and concentrated under reduced pressure. Toluene was added and the solvent removed under reduced pressure to give an oil which was used in the next transformation without further purification.

Intermediate V

To a cooled (0° C.) solution of intermediate U (2 mmol) in methylene chloride (5 ml) was added 3-ketotetradecanoic acid (997 mg), prepared by the method of Christ, et al., U.S. Pat. No. 5,530,113 and European patent application 92309057.5, followed by 1-(3-dimethylaminopropyl)-3-ethylcarbodiimide hydrochloride (1.5 g) and the mixture stirred for approximately 30 minutes. The mixture was diluted with methylene chloride (150 ml), washed with 1 N aqueous sodium hydroxide, dried (sodium sulfate) and the solvent removed under reduced pressure. Chromatography on silica followed by chromatography on basic alumina rave 1.64 g of intermediate V.

Intermediate W

A solution of intermediate V (1.45 g) in glacial acetic acid (5 ml) was added to a suspension of well stirred zinc copper couple (14 g) in acetic acid (10 ml). The mixture was stirred for 15 minutes and additional zinc/copper couple (10 g) was added. After an additional 15 minutes, the mixture was filtered through diatomaceous earth which was then washed with ethyl acetate. The combined washings were diluted with toluene and the solvent removed under reduced pressure. The residue was chromatographed on a bilayered mixture of basic alumina and silica to give intermediate W which was used without further purification.

Intermediate X

A solution of intermediate W (1.02 mmol) and cis-vaccenic acid (575 mg) was dissolved in toluene (5 ml) three times and the solvent removed under reduced pressure. The dried residue was dissolved in methylene chloride (3 ml) and !-(3-dimethylaminopropyl)-3-ethylcarbodiimide hydrochloride (780 mg) was added and the mixture stirred for 3 hours. The mixture was diluted with methylene chloride and chromatographed directly to give 734 mg of intermediate X. Further chromatography of the impure fractions gave an additional 58 mg of material.

Intermediate Y

To a solution of intermediate X (785 nag) in methylene chloride (10 ml) was added a solution of 48% aqueous hydrogen fluoride in acetonitrile (15 ml). The mixture was stirred for 90 minutes, diluted with methylene chloride (50 ml), washed with water, and with aqueous sodium bicarbonate solution. The mixture was dried (sodium sulfate) and chromatographed to give intermediate Y, 719 mg.

Intermediate Z

Intermediate Y (719 mg) was dissolved in methylene chloride and sodium sulfate (1.4 g) was added. Diallyldiisopropylphosphoramidite (189 microliters) and tetrazole (162 mg) were added, the mixture stirred for 10 minutes and then cooled to −78° C. A solution of m-chloroperoxybenzoic acid (192 mg) in methylene chloride (4 ml) was added dropwise. The mixture was washed with aqueous sodium thiosulfate and with aqueous sodium bicarbonate, dried (sodium sulfate) and the solvent removed under reduced pressure. The residue was chromatographed to give 660 mg of intermediate Z.

Compound E1

To a solution of tetrakis(triphenylphosphine)palladium (0) (166 mg) in 2 ml of tetrahydrofuran: acetic acid (10:1) mixture was added a solution of intermediate Z (660 mg) in 3 ml of the same solvent mixture. After 30 minutes, additional tetrakis(triphenylphosphine)palladium (0) was added. After an additional 1½ hours, toluene was added and the solvent removed under reduced pressure. The mixture was purified by chromatography on diethylaminoethylcellulose. The purified mixture was dissolved in 0.1 N aqueous sodium hydroxide, filtered through a 0.45 micron sterile filter 25 and purified by HPLC on a YMC-Pack ODS-AP column to give 130 mg of compound E1.

Analytical data for some of the compounds and intermediates made bar the methods described above is given below:

Compound E1: 'NMR (CD30D) 8: 5.3 (1H, m), 4.6 (1, m), 4.0 (m, m), 3.9 (1H, d),3.7 (1H, t), 3.6 (1H, t), 3.4 (3H, s), 3.3 (3 H, t), 2.6 (2H, t), 2.3 (2 H, m), 2.0 (2H, m) 1.7–1.2 (m, m), 0.9 (6H, t).

$^{31}$P NMR (CD3OD) 6. 4.71, 3.98.

Compound E1: (M+Na)=1333
Compound E2: (M+3 Na)+=1361
Compound E3: (M+3 Na)+=1365
Compound E5: (M+Na)+=1303
Compound E6: (M+Na)+=1359
Compound E7: (M+Na)+=1305
Compound E8: (M 30 3 Na)+=1393
Compound E10: (M+Na)+1425

Intermediate G: $^1$H NMR (CDCl'3) 5: d, (1H), 3.9–3.7 (m, multiple), 3.65 (t, 1H), 3.37 (s,3H), 3.2 (m,2H), 1.75 (q, 2H), 1.52 (s,3H), 1.4 (s 3H), 1.3 (broad m,multiple), 0.95 (s,9H), 0.9 (t,3H), and 0.2 (d,6H)

Intermediate H: $^1$H NMR(CDCl3) 5: 4.58 (d, 1H), 4.09 (m,2H), 3.9 (dd, 1H), 3.75 (dd, 1H), 3.7 (m, 1H), 3.5 (t, 1H), 3.37 (s,3H), 3.23 (t, 1H). 3.05 (t, 1H), 1.8 (m,2H), 1.68 (m, 1H), 1.5 (m, 1H), 1.3 (broad m,muitipie), 0.95 (s,9H), 0.9 (t,3H), 0.2 (d,6H)

Intermediate I: $^1$H NMR (CDCl3) 8:4,52 (d, 1H), 4.05 (mn,2H), 3.75 (m, 1H), 3.67 (t, 1H), 3.5 (t, 1H), 3.45 (s,3H), 3.35 (s,3H), 3.25 (t, 1H). 3.05 (t, 1H), 1.8 (m,2H), 1.65 (m, 1H), 1.5 (m, 1H), 1.3 (broad s,m), 0.95 (s,9H), 0.9 (t,3H), 0.2 (s,6H)

Intermediate J: $^1$H NMR (CDCl3) 5: 5.95 (m,2H), 5.35 (d, 1H), 5.22 (d, 1H), 4.6 (q,2H), 4.5 (d, 1H), 4.32 (q, 1H), 3.9–3.75 (m,3H), 3.7 (dd, 1H), 3.65 (dd, 1H), 3.45 (m, 1H), 3.38 (s,3H), 3.33 (s,3H), 3.27 (t, 1H), 3.2 (t, 1H), 1.9–1.75 (m,3H), 1.5 (m, 1H), 1.3 (broad m,multiple), 0.95 (s,9H), 0.9 (t,3H), 0.2 (s,6H)

Intermediate L: $^1$H NMR (CDCl3)5:5.95 (d, 1H), 5.4 (d,2H), 5.25 Z(d,2H), 4.95 (d, 1H), 4.7 (q,2H), 4.55 (q,2H), 4.32 (q, 1H), 3.9–3.75 (m,3H), 3.7 (dd, 1H), 3.65 (dd, 1H), 3.55 (m, 1H), 3.4 (m, 1H), 3.4 (s,3H), 3.3 (s,3H), 3.25 (ml 1H), 1.75 (m,multiple), 1.5–1.4 (m,2H), 1.3 (broad s,multiple). 0.95–0.9 (broad s, 12H), 0.2 (d, 6H)

Intermediate M: $^1$H NMR (CDCl3) 8: 5.95 (m, 2LI), 5.75 (d, 1H), 5.4 (d, 1H), 5.25 (d, 2H), 4.75–4.65 (dd,2H), 4.6 (q; 1H), 4.3 (q, 1H), 4.1 (2H), 3.9 (m,2H), 3.65 (m, 1H), 3.4 (s,3H), 3.25 (s,3H), 1.75 (broad m,2H), 1.55–1.4 (m,2H), 1.3 (broad s,multiple), 0.9 (t,3H)

Intermediate O; $^1$HNMR (CDCl3) 6: 4.5 (d, 1H), 3.8 (d d,1H), 3.78 (m, 2H), 3.6 (m,multiple), 3.2 (m,2H), 1.5 (s,3H), 1.4 (s,3H), 1.3 (broad s, multiple), 0.95 (s,9H), 0.9 (t,3H), 0.18 (d,6H)

Intermediate P: $^1$H NMR (CDCl3) 8: 4.5 (d, 1H), 3.75 (dd, 2H), 3.6 (q, 2H), 3.5 (t, 1H), 3.3 (m, 1H), 3.2 (t, 1H), 3.0 (t, 1H), 1.6 (m,2H), 1.25 (broad s,multiple), 0.95 (s,9H), 0.9 (t,3H), 0.18 (d,6H)

Intermediate Q: $^1$H NMR (CDCl3) 8: 4.5 (d, 1H), 3.82 (t, 2H), 3.7 (m, 2H), 3.6 (t, 1H), 3.3(m, 1H), 3.2 (t, 1H), 3.05 (q,2H), 1.6 (m,2H), 1.3 (broad s,multiple), 0.95 (s,9H), 0.88 (s,9H), 0.85 (t,3H), 0.2 (d,6H), 0.1 (d,6H)

Intermediate R: $^1$H NMR (CDCl3) 5: 5.9 (m, 1H), 5,4–5-25 (dd,2H), 4.75 (t, 1H), 4.6(d,2H), 4.45 (d, 1H), 3.75 (q, 1H), 3.7 (d,2H), 3.53 (q, 1H), 3.38 (m, 1H), 3.25 (t, 1H), 3.15 (t, 1H), 1.5 (t,2H), 1.25 (s, multiple), 0.95(s,9H), 0.85 (1 2H), 0.2 (s,6H), 0.07 (s,6H)

Intermediate S: $^1$H NMR (CDCl3) 5: 5.9 (m, 1H), 5.4–5.25 (dd,2H), 4.75 (t, 1H), 4.6 (d,2H), 4.52 (d, 1H), 3.7 (m,multiple), 3.65–3.6 (dd,2H), 3.55 (q, 1H), 3.4 (m, 1H), 3.28 (t, 1H), 3.2 (t, 1H), 1.5 (t,2H), 1.3 (s, multiple), 0.9 (s,9H), 0.85 (t,3H), 0.2 (s,6H)

Intermediate T: $^1$H NMR (CDCl3) 6: 5.9 (m, 3H), 5.6 (d, 1H), 5.4–5.2 (m, 6H), 4.8 (d, 1H), 4.7–4.6 (m, 2H), 4.5 5 (q, 1H), 4.5 (d, 1H), 4.3 q, 1H), 3.8–3.7 (m, multiple), 3.6 (dd, 1H), 3.5 (m,multiple), 3.35 (s,3H), 3.2 (s,3H), 3.15 (t, 1H), 1.7 (m,2H), 1.5 (m,2H) 1.3 (s,multiple), 0.95 (t,6H), 0.2 (t,6H)

Intermediate V: $^1$H NMR (CDCl3)6:7.3 (d, 1H), 5.95 (m,3H), 5.6 (d, 1H), 5.4–5.2 (m,6H), 4.95 (d, 1H), 4.8 (d, 1H), 4.7–4.5 (m,multiple)4.3 (q, 1H), 3.9–3.65 (m,multiple), 3.6 (m,multiple), 3.45 (t, 1H), 3.4 (t,3H), 3.35 (s,2H), 3.28 (3H), 2.5 (t,2H), 1.8 (m,2H), 1.6 (m,2H), 1.45 (m,2H), 1.3 (broad s,multiple), 0.95–0.8 (m, 1H), 0.15 (d,6H)

Intermediate X: $^1$H NMR (CDCl3) 8:7.3 (d, 1H), 5.95 (m,4H), 5.4–5.2 (m,8H), 4.95 (d, 1H), 4.8 (d, 1H), 4.7 (t, 1H), 4.6 (d, 1H), 4.55 (q, 1H), 4.3 (q, 1H), 4.1 (t, 1H) 3.9 (q, 1H) 3.8 (t, 1H), 3.7–3.5 (m,multiple) 3.45(t, 1H), 4.35 (s,3H), 3.3 (s,2H), 3.28 (s,3H), 2.5 (t,2H), 2.2 (t, 1H), 2 (d, 1H), 1.7 (q,2H), 1.6 (m,2H), 1.3 (s,multiple), 0.95–0.8 (m,21), 0.15 (d,6H)

Intermediate Y: $^1$H NMR (CDCl3) 5: 6.65 (d, 1H), 6.55 (d, 1H), 5.905 (m,5H). 5.7 (m, 1H), 5.4–5.2 (m, 1 2H). 4.8 (m,2H), 4.6 (d, 1H), 4.5 (m, 1 OH), 4.3 (q, 1H), 4.1 (m, 1H), 3.85–3.45 (m,multiple), 3.4 (s,3H), 3.35 (s,3H), 3.25 (s,3H), 3.2 (t, 1H), 2.5 (dd,2H), 2.2 (t,2H), 2 (m,mutiple), 1.7–1.2 (m,mutiple), 0.9 (t,12H).

Example 2

Synthesis of Compound E21

The preparation of a preferred alternate compound of this invention, compound E21 and its related analogs, is shown below. As one of ordinary skill in the art would easily understand, use of alternative starting materials will provide alternate compounds of the invention. For example use of side chain starting materials of different chain lengths will provide compounds of the invention with side chains of varying lengths. The detailed synthetic procedure for the preparation of compound E21 may be found in Example 2 of the application.

A representative preparation of the "left" portion of compound E2 1 is outlined below. Compound 58 is made from compound 57 according to Christ, U.S. Pat. No. 5,530,113 and EP 92309057.5 or from the intermediate F in a manner analogous to that described above for the synthesis of intermediate J from intermediate F except that a different side chain is attached to the C-3 alcohol:

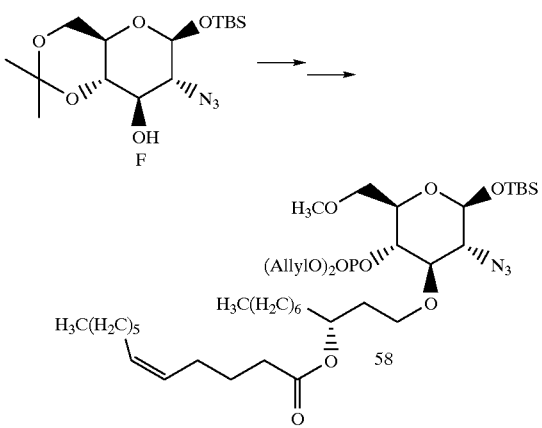

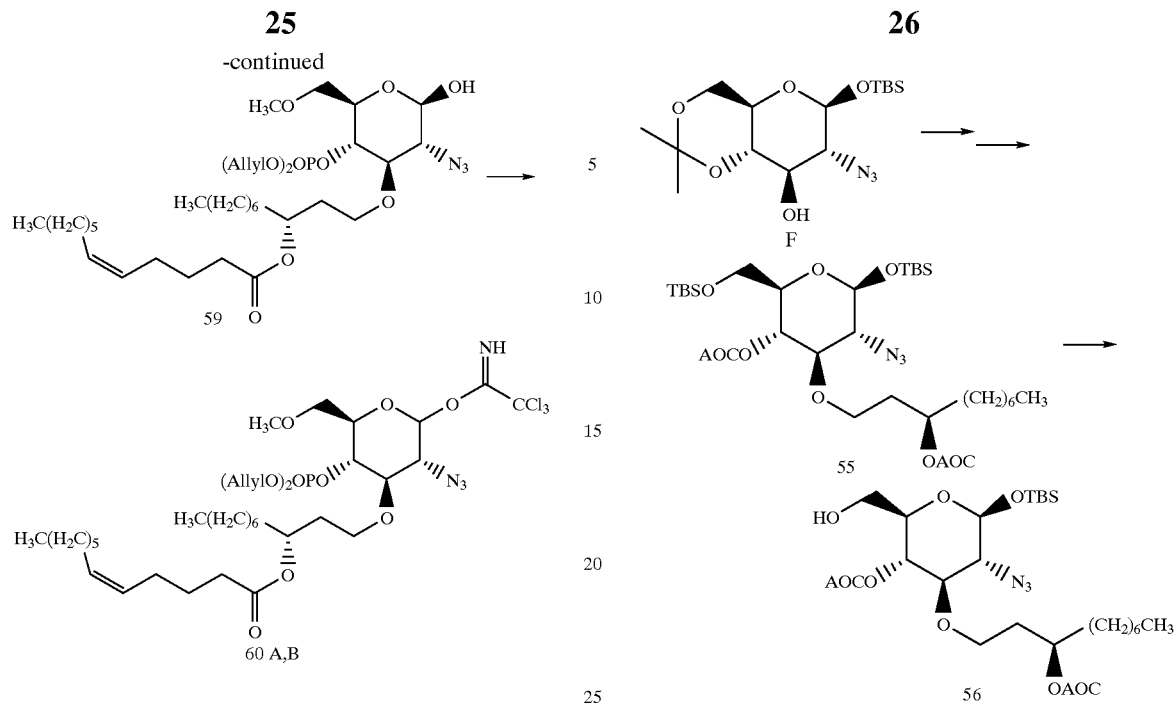

A representative synthesis of the "right" portion of compound E21 is shown below. Compound 55 is made from intermediate F in a manner analogous to that shown above for the synthesis of intermediate R from intermediate F except that a different side chain is attached to the C-3 alcohol.

These two "halves" of the molecule are then coupled as outlined below and further elaborated to give compound E21.

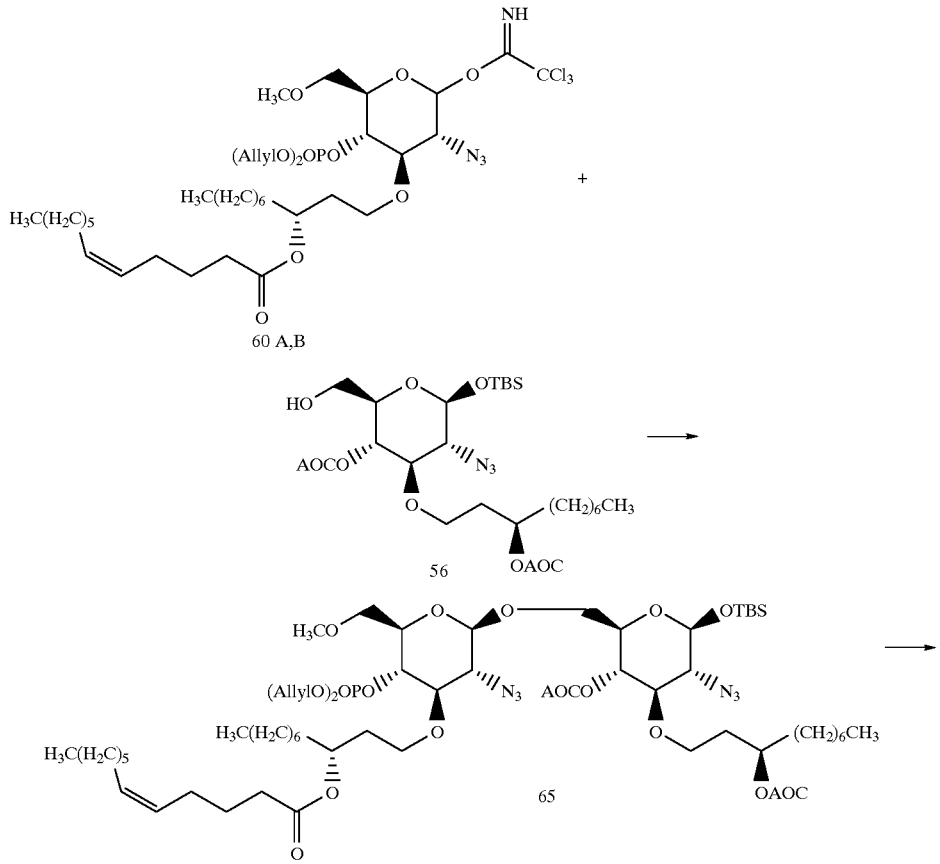

-continued
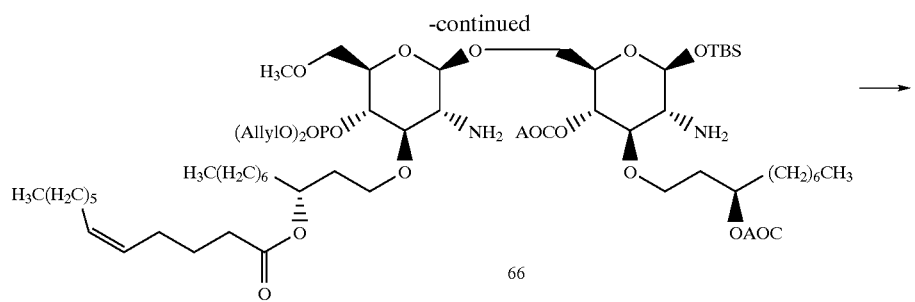
66
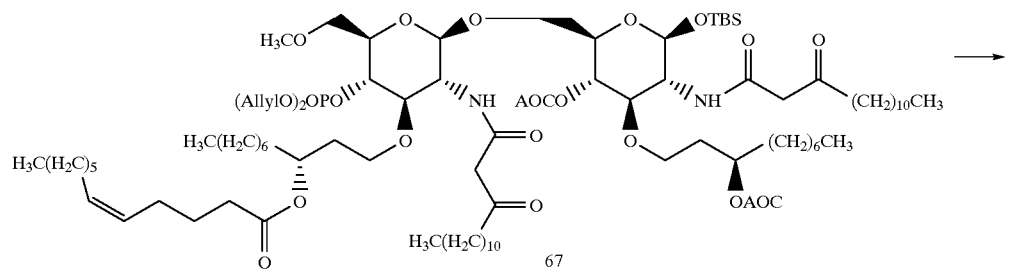
67
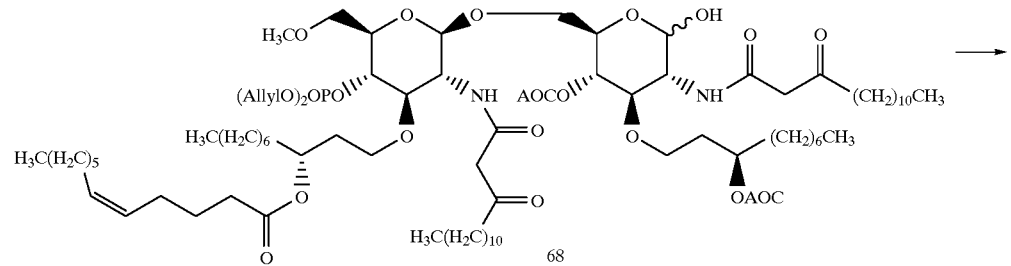
68
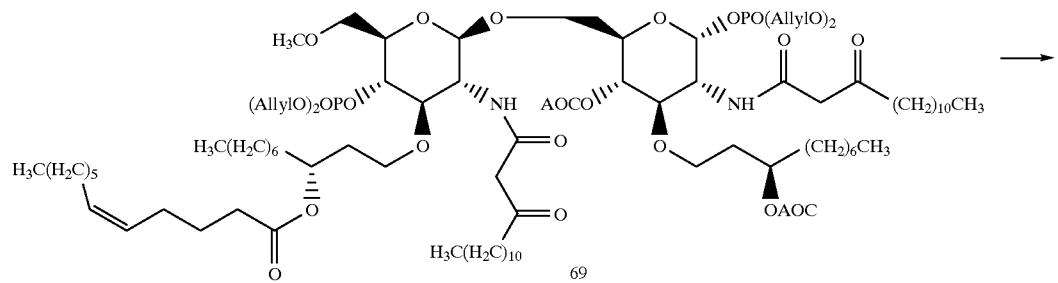
69
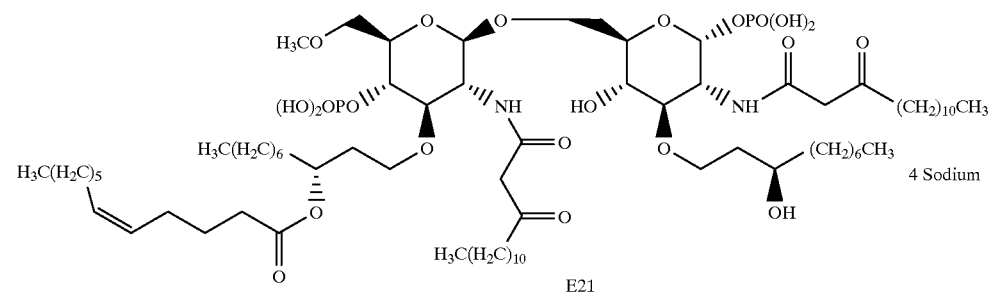
E21

Compound 57 is used as a starting material, and is obtained according to the methods of Christ et al., disclosed in U.S. Pat. No. 5,530,113 and EP 92309057.5, both of which are incorporated by reference herein.

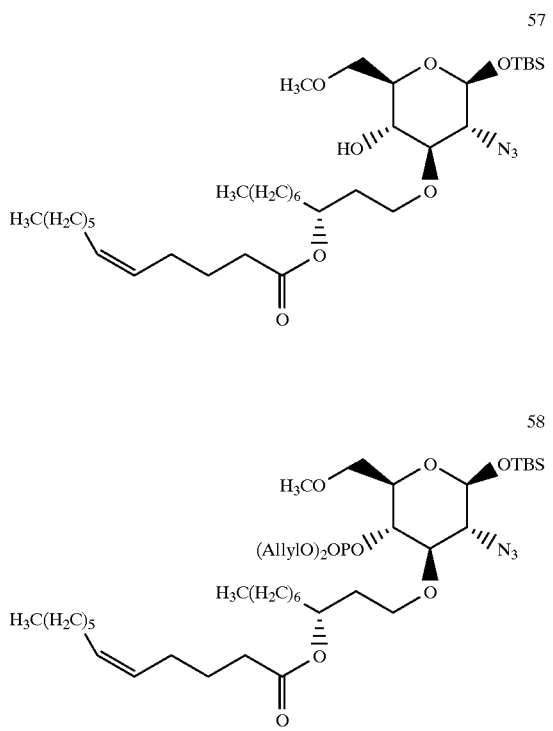

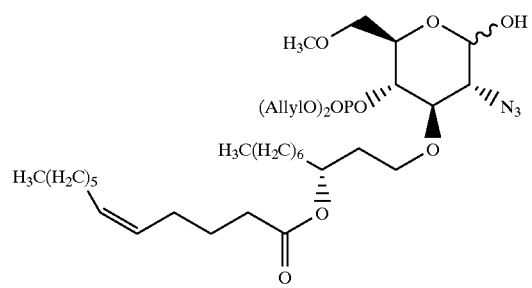

To a magnetically stirred solution of Compound 57 (8.7 g; 0.013 mol) dissolved in 46 ml anhydrous dichloromethane, at room temperature, under a nitrogen atmosphere, was first added 4.8 ml (0.02 mol) bis(allyloxy) (diisopropylamino) phosphine and then added (in one portion) 4.1 g (0.06 mol) 1 H-tetrazole. After five minutes, the reaction mixture was cooled to $-78°$ C., and a solution of 3.35 g (0.02 mol) 55% 3-chloroperoxybenzoic acid dissolved in 37 ml anhydrous dichloromethane was added dropwise over a 10 minute period. The reaction was then quenched at $-78°$ C. by the addition of 100 ml saturated aqueous sodium bicarbonate solution. The resulting mixture was then extracted with 500 ml dichloromethane and the organic layer extract washed first with 200 ml water, then with 200 ml saturated aqueous sodium chloride solution, and dried over 300 g sodium sulfate. Concentration under reduced pressure at room temperature provided the crude product which was purified on a silica gel (1 kg) column and eluted with ethyl acetate:hexanes (1:6 (v/v)). Evaporation of solvent from the product-containing fractions (as identified by thin layer chromatographic analysis) under reduced pressure at room temperature and drying overnight under vacuum at room temperature provided 8.8 g (0.011 mol) of compound 58. Rf: 0.28 (ethyl acetate:hexanes, 1:4 (v/v)) in an 85% yield.

To a magnetically stirred solution of 80 ml 6M hydrogen fluoride in acetonitrile in a Teflon reaction vessel was added at room temperature, 8.8 g (10.6 mmol) of compound 58 dissolved in 30 ml of dichloromethane. The resulting mixture was stirred for nine hours, poured into 200 ml saturated aqueous sodium bicarbonate solution at 0° C., and extracted with 300 ml dichloromethane. The organic layer extract was washed with 100 mL saturated aqueous sodium chloride solution, dried over 100 g sodium sulfate, filtered and concentrated under reduced pressure at room temperature. The residue was then purified on a silica gel (1 kg) column and eluted with hexanes:ethyl acetate (1:1 (v/v)). Evaporation of solvent from the product-containing fractions (as identified by thin layer chromatographic analysis) under reduced pressure at room temperature and drying overnight under vacuum at room temperature provided 5.7 g (7.95 mmol) of Compound 59. Rf: 0.37 (dichloromethane:methyl alcohol, 95:5 (v/v))) in 75% yield.

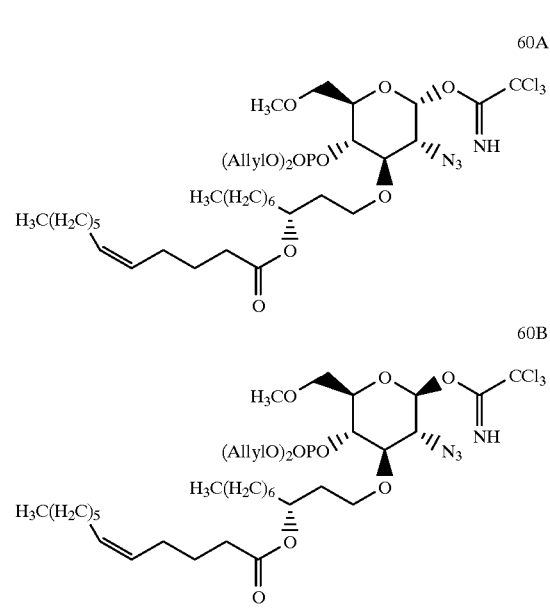

To a mechanically stirred solution of 10.32 g (14.5 mmol) of Compound 59 in 200 ml trichloroacetonitrile, 8.80 g (63.7 mmol) of potassium carbonate was added at room temperature under nitrogen. After 20 minutes, the mixture was filtered through 100 g Celite 545, the filtered solids washed with 100 ml dichloromethane and the combined filtrates concentrated under reduced pressure at room temperature. The crude product obtained was purified on a silica gel (10 g) column by elution with hexanes: ethyl acetate (1 :I(v/v)). Evaporation of solvent from the product containing fractions (identified by thin layer chromatographic analysis) under reduced pressure at room temperature and drying overnight under vacuum at room temperature gave 6.7 g (7.8 mmol) of 60B (β isomer). Rf: 0.61 (hexanes:ethyl acetate, 1:1 (v/v))) and 4.4 g (5.1 mmol) of 60B (α isomer). Rf: 0.53 (hexanes:ethyl acetate, 1:1 (v/v))) in a combined yield of 89%.

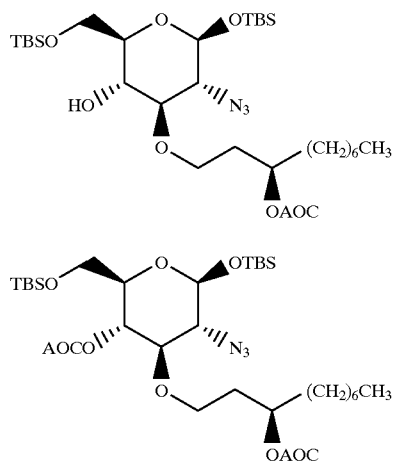

To a mechanically stirred solution of Compound 54 (8.9g; 13.2 mmol) obtained according to Christ et al., U.S. Pat. No. 5,530,113 and EP 92309057.5, dissolved in 270 ml of anhydrous toluene and 4.2 ml of anhydrous pyridine, at 0° C., under a nitrogen mosphere, was slowly added 10.2 ml (26.4 mmol) of 1.93 M phosgene in toluene, over a 10-minute period. Twenty minutes later, 8 ml (105.6 mmol) of allyl alcohol was added over a five-minute period and the resulting reaction mixture was stirred for an additional 15 minutes. The reaction mixture was quenched with 200 ml saturated aqueous sodium bicarbonate solution, diluted with 1 L ethyl acetate, and the organic layer separated, and washed with 500 ml water and then 500 ml saturated aqueous sodium chloride solution, dried over 500 g sodium sulfate, filtered, and concentrated under reduced pressure at room temperature. The residue was purified on a silica gel (1 kg) column and eluted with ethyl acetate: hexanes (1:19 (v/v)). Evaporation of solvent from the product-containing fractions (as identified by thin layer chromatographic analysis) under reduced pressure at room temperature and drying overnight under vacuum at room temperature provided 9.5 g (12.5 mmol) of Compound 55. Rf: 0.68 (ethyl acetate:heaxanes, 1:9(v/v))) in 95% yield.

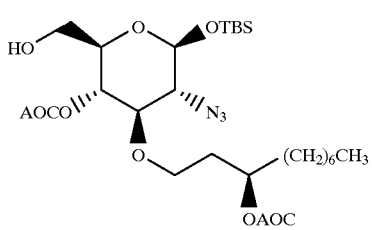

In a 1 L Teflon reaction vessel, Compound 55 (5.8 g; 7.6 mmol) was dissolved in 200 ml of dichloromethane. To the solution at room temperature, with magnetic stirring was added 150 ml of a 1M solution of hydrofluoric acid in acetonitrile. After seven hours, the reaction mixture was quenched by pouring into 200 ml saturated aqueous sodium bicarbonate solution, at 0° C., and extracted with 500 ml dichloromethane. The organic layer was separated, washed with 100 ml water then with 100 ml saturated aqueous sodium chloride solution, dried over 300 g sodium sulfate, filtered, and concentrated under reduced pressure at room temperature. The residue obtained was purified on a silica gel (600 g) column and eluted with ethyl acetate:hexanes (1:4 (v/v)). Evaporation of solvent from the product-containing fractions (as identified by thin layer chromatographic analysis) under reduced pressure at room temperature and drying overnight, under vacuum, at room temperature provided 4.5 g (6.7 mmol) of compound 56. Rf: 0.33 (ethyl acetate:hexanes,1:4 (v/v))) in 88% yield.

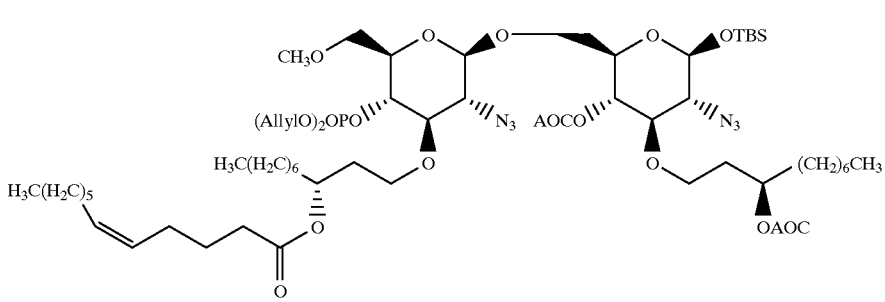

A mixture of 7.35 g (8.5 mmol) of Compound 60 (αβ mixture) and 5 g (7.4 mmol) of Compound 56 which had been dried under vacuum for 14 hours, was dissolved in 200 ml of anhydrous dichloromethane. To this solution was added 8.2 g of powdered AW-300 molecular sieves (previously flame-dried under vacuum) and the resulting mixture magnetically stirred for one hour at room temperature under argon. The mixture was then cooled to −35° C., and 8.7 ml (0.50 mmol) of a 0.2 M trimethylsilylmethyl trifluoromethanesulfonate (Aldrich Chemical Co.) :dichloromethane solution (prepared by dissolving 310 μL (2.03 mmol) of trimethylsilylmethyl trifluoromethanesulfonate in 40 ml of anhydrous dichloromethane and stirring with I g powdered AW-300 molecular sieves for one hour at room temperature) was slowly added over an eight hour period. The reaction was quenched with 100 ml of saturated aqueous sodium bicarbonate solution, then diluted with 500 ml dichloromethane, and filtered through 50 g Celite 545. The filtrate was then washed with 100 ml portions of saturated aqueous sodium bicarbonate solution, water, and saturated aqueous sodium chloride solution sequentially, dried over 100 g sodium sulfate, filtered, and then concentrated under reduced pressure at room temperature. The resulting residue was purified on a silica gel (200 g) column by elution with ethyl acetate and hexanes (1:4 (v/v)). Evaporation of solvent from the product containing fractions (identified by use of thin layer chromatography analysis) under reduced pressure at room temperature and drying overnight under vacuum at room temperature gave 8.1 g (0.006 mol) of Compound 65. Rf: 0.42 (ethyl acetate:hexanes, 1:2(v/v))) in 82% yield.

To a magnetically stirred solution of Compound 66 (1.72 g; 1.33 mmol) in 10 ml anhydrous dichloromethane, at 0° C., was added 1.83 g (8.88 mmol) of 1,3dicyclohexylcarbodiimide and 1.1 g (4.44 mmol) of Compound D2

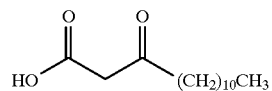

obtained according to Christ et al., U.S. Pat. No. 5,530,113 and EP 92309057.5 or by conventional methods. After 30 minutes, when thin layer chromatographic analysis (dichloromethane:methyl alcohol, 95:5 (v/v)) indicated that the reaction was complete, the reaction mixture was diluted with 50 ml ethyl acetate, filtered through 10 g Celite 545, the solids washed with 20 ml ethyl acetate, and the filtrate concentrated under reduced pressure at room temperature to yield a syrupy residue. The crude syrup was dissolved in 5 ml dichloromethane, loaded onto a silica gel (100 g) column and eluted initially with a 1:4 (v/v) mixture of ethyl acetate:hexanes to remove reagent residues and then with a 1:2 (v/v) mixture of ethyl acetate:hexanes. Evaporation of solvent from the product containing fractions (as identified by thin layer chromatographic analysis) under reduced pressure at room temperature and drying overnight under vacuum at room temperature provided 1.82 g (1.04 mmol) of Compound 67. Rf: 0.54 (dichloromethane:methyl alcohol, 95:5 (v/v))) in 71% yield.

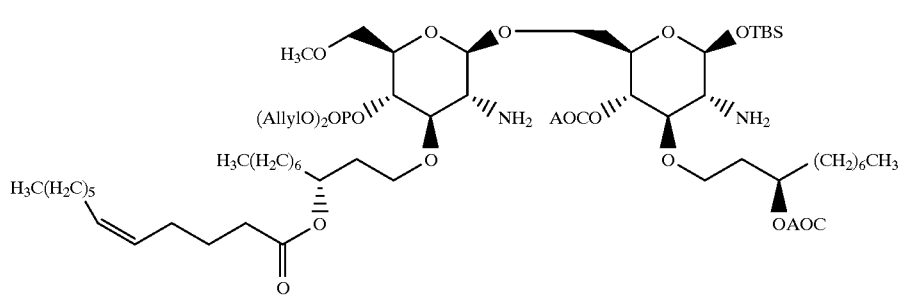

To a magnetically stirred solution of compound 65 (1.99 g; 1.48 mmol) dissolved in 10 ml of anhydrous dichloromethane was added 250 mg (0.45 mmol) of tin(II)trisbenzenethiolate triethylamine complex and the resulting mixture stirred at room temperature under a nitrogen atmosphere in the absence of light for 30 minutes, at which time thin layer chromatographic analysis (hexanes:ethyl acetate, 1:1(v/v)) indicated starting material to be consumed. The reaction mixture was loaded directly into a silica gel (10 g) column and eluted first with a 4:1 (v/v) mixture of hexanes::ethyl acetate to remove reagent by-products and then with ethyl acetate. Evaporation of solvent from the product-containing fractions (as identified by thin layer chromatographic analysis) under reduced pressure at room temperature and drying under vacuum at room temperature for 30 minutes provided partially purified Compound 66 (1.72 g (1.33 mmol)). Rf: 0.48 (dichloromethane:methyl alcohol, 95:5(v/v)l) which was suitable for use in subsequent reaction in 90% yield.

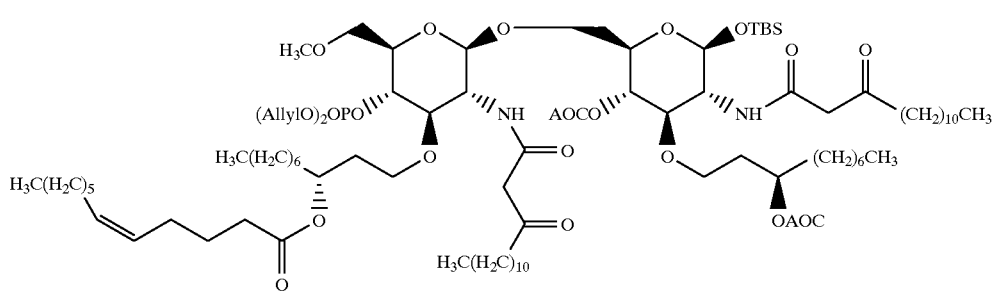

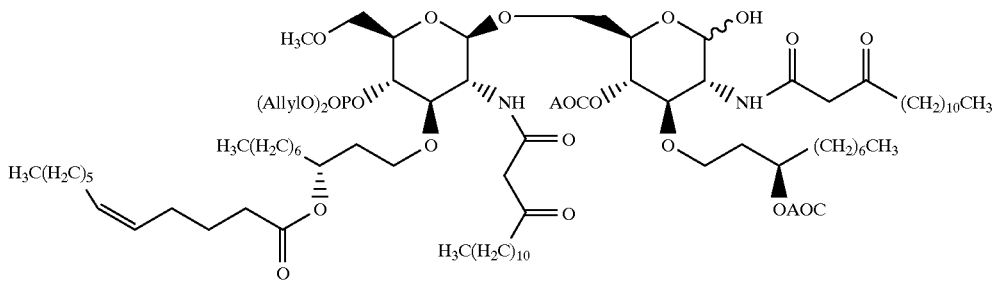

68

To a magnetically stirred solution of 8 ml 6 M hydrogen fluoride in acetonitrile in a Teflon reaction vessel was added 390 mg (0.224 mmol) of Compound 67 dissolved in 0.5 ml of dichloromethane, at room temperature. The mixture was stirred for one and a half hours, diluted with 20 ml saturated aqueous sodium bicarbonate solution, and extracted with 100 ml dichloromethane. The organic layer extract was washed first with 20 ml water, and then with 10 ml saturated aqueous sodium chloride solution, dried over 25 g sodium sulfate. filtered and concentrated under reduced pressure at room temperature. The residue was purified on a silica gel (50 g) column and eluted with dichloromethane:methyl alcohol (98:2 (v/v). Evaporation of solvent from the product-containing fractions (as identified by thin layer chromatographic analysis) under reduced pressure at room temperature and drying overnight under vacuum at room temperature provided 325 mg (0.20 mmol) of Compound 68. Rf: 0.34 (dichloromethane and methyl alcohol, 95:5 (v/v)) in 89% yield.

100 μL dichloromethane was added, and the mixture was stirred for 20 additional minutes. A 0.5 ml saturated aqueous sodium bicarbonate solution was then added, and the resultant mixture extracted with 10 ml dichloromethane. The organic layer was separated and washed first with 10 ml water and then with 5 ml saturated aqueous sodium chloride solution, and dried over 5 g sodium sulfate. Concentration of the dried organic extract under reduced pressure at room temperature provided the crude product which was purified on a silica gel (10 g) column and eluted with ethyl acetate:chloroformn (1:1(v/v)). Evaporation of solvent from the product-containing fractions (as identified by thin layer chromatographic analysis) under reduced pressure at room temperature and drying for one hour under vacuum at room temperature provided 41.7 mg (0.023 mmol) of Compound 69. Rf: 0.40 (dichloromethane:methyl alcohol, 95:5 (v/v)) in a 78% yield.

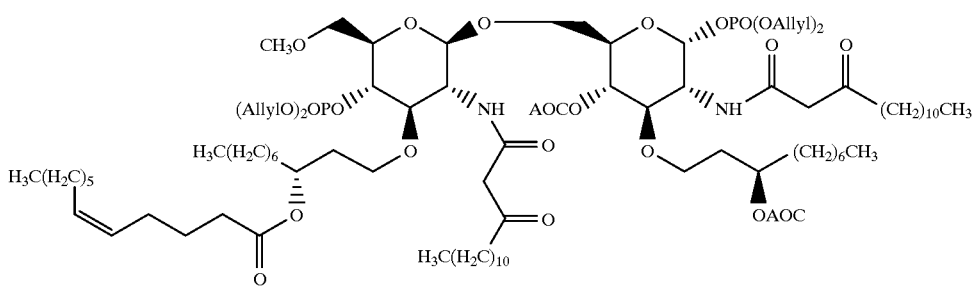

69

To a magnetically stirred solution of 50 mg (0.03 mmol) of Compound 68 in 1 ml anhydrous dichloromethane was first added 11.3 mg (0.045 mmol) bis(allyloxy) (diisopropylamino) phosphine followed by 9.4 mg (0.135 mmol) 1H-tetrazole at 0° C., under a nitrogen atmosphere. The resulting mixture was warmed to room temperature, stirred 20 minutes, cooled to −78° C., and a solution of 9.5 mg (0.036 mmol) 3-chloroperoxybenzoic acid dissolved in

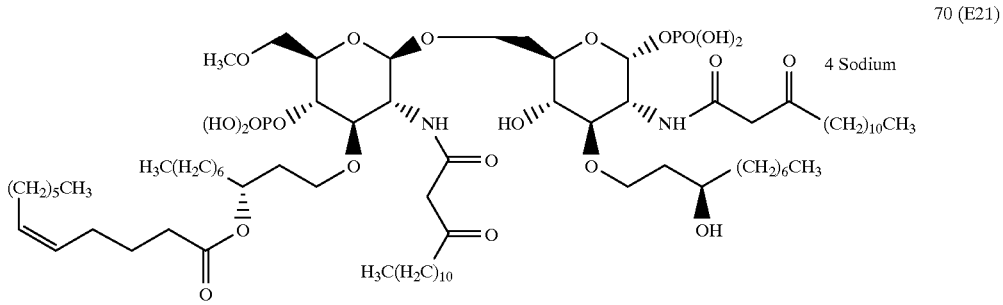

70 (E21)

To a solution of Compound 69 (130 mg, 0.072 mmol) dissolved in 10 ml tetrahydrofuran:96% formic acid (10:1 (v/v)), under a nitrogen atmosphere, in the absence of light, was added 843 mg (0.72 mmol) tetrakis(triphenylphosphine) palladium(O) and 575 mg (2.19 mmol) triphenylphosphine. The resulting mixture was stirred for a total of one hour, and concentrated under reduced pressure at room temperature. The resulting residue was mixed with 5 ml of toluene and evaporated under reduced pressure at room temperature to a thick paste, suspended in 10 ml methyl alcohol, and hydrogen sulfide gas bubbled through the solution for several minutes. The solvent was removed by evaporation under reduced pressure at room temperature and the crude product was taken up in 10 ml of a 3:2:1 (v/v/v) mixture of methyl alcohol:chloroform:water and filtered through a 0.2 μ Teflon HPLC filter (Rainin instrument Co.). The filtrate was loaded onto a DEAE-celluose (100 g (Sigma Chemical Co.)) column and eluted with 2 L of a 3:2:1 (v/v/v) mixture of methyl alcohol:chloroform:water, using a 0 to 0.1 M ammonium acetate linear salt gradient. The purified product-containing fractions (as identified by thin layer chromatographic analysis) were combined and an equal volume of chloroform was added. The organic layer was separated and concentrated under reduced pressure at room temperature to yield the purified product as the ammonium salt. The product was taken up in 100 ml water and lyophilized to remove remaining traces of ammonium acetate. The lyophilized product was suspended in 40 ml of water, stirred with 6 g of chelex-100 resin (sodium form) (Bio-Rad Laboratories, Hercules, Calif.), passed through a 10 g column of Chelex-100 resin (sodium form), and eluted with 20 ml of water. The solution was filtered through a 0.2 μ Teflon HPLC filter (Rainin Instrument Co.) and lyophilized to provide 98 mg (0.063 mmol) of the tetrasodium salt, i.e., Compound 70. Rf: 0.60 (chloroform:methyl alcohol:glacial acetic acid:water, 125:75:10:20 (v/v/v/v)), as a white hygroscopic foam in 87% yield.

Compound 70 is the Lipid A analog E21 of this invention.

Example 3

Preferred Compounds

Some representative compounds of the present invention, including preferred compounds E1, E20, and E21, are referred to by compound number according to the tables below which indicate the structure of the side chains of a given compound.

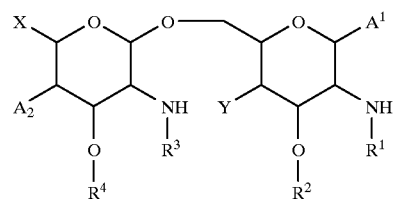

Formula 1

| Compound # | $A^1/A^2$ | $R^1$ | $R^2$ |
|---|---|---|---|
| E1 | $OPO(OH)_2$ | $COCH_2CO(CH_2)_{10}CH_3$ | $(CH_2)_9CH_3$ |
| E2 | $OPO(OH)_2$ | $COCH_2CO(CH_2)_{10}CH_3$ | $(CH_2)_9CH_3$ |
| E3 | $OPO(OH)_2$ | $COCH_2CO(CH_2)_{10}CH_3$ | $(CH_2)_9CH_3$ |
| E4 | $OPO(OH)_2$ | $COCH_2CH(OH)(CH_2)_{10}CH_3$ | $(CH_2)_9CH_3$ |
| E5 | $OPO(OH)_2$ | $COCH_2CO(CH_2)_{10}CH_3$ | $(CH_2)_9CH_3$ |
| E6 | $OPO(OH)_2$ | $CO(CH_2)_9CH=CH(CH_2)_5CH_3$ | $(CH_2)_9CH_3$ |
| E7 | $OPO(OH)_2$ | $CO(CH_2)_{12}CH_3$ | $(CH_2)_9CH_3$ |
| E8 | $OPO(OH)_2$ | $COCH_2CH(OCH_3)(CH_2)_{10}CH_3$ | $(CH_2)_9CH_3$ |
| E9 | $OPO(OH)_2$ | $COCH_2CH(OCH_3)(CH_2)_{10}CH_3$ | $(CH_2)_9CH_3$ |
| E10 | $OPO(OH)_2$ | $COCH_2CH(OH)(CH_2)_{10}CH_3$ | $(CH_2)_9CH_3-$ |
| E11 | $OPO(OH)_2$ | $COCH_2CO(CH_2)_{10}CH_3$ | $COCH_2CH(OH)(CH_2)_6CH_3$ |
| E12 | $OPO(OH)_2$ | $COCH_2CO(CH_2)_{10}CH_3$ | $CH_2CH_2CH(OH)(CH_2)_6CH_3$ |
| E13 | $OPO(OH)_2$ | $COCH_2CO(CH_2)_{10}CH_3$ | $CH_2CH_2CH(OH)(CH_2)_6CH_3$ |
| E14 | $OPO(OH)_2$ | (R) $COCH_2SO(CH_2)_{10}CH_3$ | $CH_2CH_2CH(OH)(CH_2)_6CH_3$ |
| E15 | $OPO(OH)_2$ | (R) $COCH_2SO(CH_2)_{10}CH_3$ | $CH_2CH_2CH(OH)(CH_2)_6CH_3$ |

-continued

| | | | |
|---|---|---|---|
| E16 | $OPO(OH)_2$ | (R) $COCH_2SO(CH_2)_{10}CH_3$ | $CH_2CH_2CH(OH)(CH_2)_6CH_3$ |
| E17 | $OPO(OH)_2$ | (R, S) $COCH_2SO(CH_2)_{10}CH_3$ | $CH_2CH_2CH(OH)(CH_2)_6CH_3$ |
| E18 | $OPO(OH)_2$ | (R) $COCH_2SO(CH_2)_{10}CH_3$ | $CH_2CH_2CH(OH)(CH_2)_6CH_3$ |
| E19 | $OPO(OH)_2$ | (R) $COCH_2SO(CH_2)_{10}CH_3$ | $CH_2CH_2CH(OH)(CH_2)_7CH_3$ |
| E20 | $OPO(OH)_2$ | $COCH_2CO(CH_2)_{10}CH_3$ | $CH_2CH_2CH(OH)(CH_2)_7CH_3$ |
| E21 | $OPO(OH)_2$ | $COCH_2CO(CH_2)_{10}CH_3$ | $CH_2CH_2CH(OH)(CH_2)_6CH_3$ |

| Compound # | $R^3$ | $R^4$ | X | Y |
|---|---|---|---|---|
| E1 | $CO(CH_2)_9CH=CH(CH_2)_5CH_3$ | $(CH_2)_2CH(OCH_3)(CH_2)_6CH_3$ | $CH_2OCH_3$ | OH |
| E2 | $CO(CH_2)_9CH=CH(CH_2)_5CH_3$ | $(CH_2)_2CH(OH)(CH_2)_6CH_3$ | $CH_2OCH_3$ | OH |
| E3 | $CO(CH_2)_{16}CH_3$ | $(CH_2)_2CH(OH)(CH_2)_6CH_3$ | $CH_2OCH_3$ | OH |
| E4 | $CO(CH_2)_9CH=CH(CH_2)_5CH_3$ | $(CH_2)_2CH(OH)(CH_2)_6CH_3$ | $CH_2OCH_3$ | OH |
| E5 | $CO(CH_2)_9CH=CH(CH_2)_5CH_3$ | $(CH_2)_9CH_3$ | $CH_2OCH_3$ | OH |
| E6 | $CO(CH_2)_9CH=CH(CH_2)_5CH_3$ | $(CH_2)_2CH(OH)(CH_2)_6CH_3$ | $CH_2OCH_3$ | OH |
| E7 | $CO(CH_2)_9CH=CH(CH_2)_5CH_3$ | $(CH_2)_2CH(OH)(CH_2)_6CH_3$ | $CH_2OCH_3$ | OH |
| E8 | $CO(CH_2)_9CH=CH(CH_2)_5CH_3$ | $(CH_2)_2CH(OCH_3)(CH_2)_6CH_3$ | $CH_2OCH_3$ | OH |
| E9 | $CO(CH_2)_9CH=CH(CH_2)_5CH_3$ | $(CH_2)_2CH(OH)(CH_2)_6CH_3$ | $CH_2OCH_3$ | OH |
| E10 | $CO(CH_2)_9CH=CH(CH_2)_5CH_3$ | $(CH_2)_2CH(OCH_3)(CH_2)_6CH_3$ | $CH_2OCH_3$ | OH |
| E11 | $COCH_2CO(CH_2)_{10}CH_3$ | $COCH_2CH(O-Do)(CH_2)_6CH_3$ | $CH_2OCH_3$ | OH |
| E12 | $COCH_2CO(CH_2)_{10}CH_3$ | $COCH_2CH(O-Do)(CH_2)_6CH_3$ | $CH_2OCH_3$ | OH |
| E13 | $COCH_2CO(CH_2)_{10}CH_3$ | $COCH_2CH(O-Do)(CH_2)_6CH_3$ | $CH_2OH$ | OH |
| E14 | (R) $COCH_2SO(CH_2)_{10}CH_3$ | $COCH_2CH(O-Do)(CH_2)_6CH_3$ | $CH_2OCH_3$ | OH |
| E15 | (R) $COCH_2SO(CH_2)_{10}CH_3$ | $COCH_2CH(O-Do)(CH_2)_6CH_3$ | $CH_2OH$ | OH |
| E16 | (R) $COCH_2SO(CH_2)_{10}CH_3$ | $CH_2CH_2CH(O-Do)(CH_2)_6CH_3$ | $CH_2OCH_3$ | OH |
| E17 | (R, S) $COCH_2SO(CH_2)_{10}CH_3$ | $CH_2CH_2CH(O-Do)(CH_2)_6CH_3$ | $CH_2OH$ | OH |
| E18 | (R) $COCH_2SO(CH_2)_{10}CH_3$ | $CH_2CH_2CH(O-Do)(CH_2)_6CH_3$ | $CH_2OH$ | OH |
| E19 | (R) $COCH_2SO(CH_2)_{10}CH_3$ | $CH_2CH_2CH(O-Do)(CH_2)_6CH_3$ | $CH_2OCH_3$ | OH |
| E20 | $COCH_2CO(CH_2)_{10}CH_3$ | $CH_2CH_2CH(O-Do)(CH_2)_6CH_3$ | $CH_2OCH_3$ | OH |
| E21 | $COCH_2CO(CH_2)_{10}CH_3$ | $CH_2CH_2CH(O-Do)(CH_2)_6CH_3$ | $CH_2OCH_3$ | OH |

Do = $CO(CH_2)_3CH=CH(CH_2)_5CH_3$

Example 4

Formulations

Lipid A analogs are administered in dosages which provide suitable inhibition of LPS activation of target cells. Generally, these dosages are preferably between 0.01–50 mg/patient per day, more preferably, between 0.05–25 mg/patient per day and most preferably, between 0.1–9 mg/patient per day. Repeated administration may be indicated, depending on the patient and the severity of the disease. It will be understood that the specific dose level for any particular patient will depend on a variety of factors including the activity of the specific compound employed; the age, body weight, general health, and sex of the individual being treated; the time and route of administration; the rate of excretion; other drugs which have previously been administered; and the severity of the alcoholic liver disease. The preferred route of administration is by intravenous infusion. Other suitable routes of administration will be apparent to persons of ordinary skill in the art.

Pharmaceutical compositions containing the active ingredient may be in any form suitable for the intended method of administration. Pharmaceutically acceptable salts include Tris salts, lysine salts, ammonium salts, and sodium salts.

Aqueous suspensions of the invention contain the active materials in admixture with excipients suitable for the manufacture of aqueous suspensions.

Such excipients include a suspending agent, such as sodium carboxymethyl cellulose, methyl cellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known alt for example using those suitable dispersing or wetting agents and suspending agents which lave been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

Compounds E1, E20, and E21 are particularly preferred.

Example 5

Endotoxin mediated increases in internal ($Ca^{2+}$) in Kupffer cells are blocked by endotoxin antagonists Kupffer cells are activated by increases in cytosolic $Ca^{2+}$ concentration (Decker, 1990), and chronic ethanol treatment makes $Ca^{2+}$ channels in Kupffer cells easier to open (Goto, M. et al., J. Pharmacol. Exp. Ther. 267:1264–1268 (1993)). $(Ca^{2+})_i$ can be measured fluorometrically using the fluorescent calcium indicator dye fura-2 and a microspectrofluorometer (Photon Technology International, South Brunswick, N.J.) interfaced with an inverted microscope (Nikon, Japan).

Kupffer cells were isolated by collagenase digestion and differential centrifugation using Percoll (Pharmacia, Uppsala, Sweden) as described elsewhere with slight modifications (Pertoft, H., and B. Smedsrod. In: Cell Separation, Methods and Selected Applications. Vol. 4. T. G. Pretlow II, and T. P. Pretlow, editors. Academic Press. 1–24 (1987)). Cells were cultured for 24–48 hr prior to experiments. For experiments, cells were incubated in modified Hanks' buffer (115 mM NaCl, 5 mM KCl, 0.3 mM $Na_2HPO_4$, 0.4 mM $KH_2PO_4$, 5.6 mM glucose, 0.8 mM $MgSO_4$, 1.26 mM $CaCl_2$, 15 mM HEPES, pH 7–4) containing 5 µM fura-2/acetoxymetyl ester (Molecular Probes Inc., Eugene, Oreg.) and 0.03% Pluronic F127 (BASF Wyandotte, Wyandotte, Mich.) at room temperature for 60 min. Coverslips plated with Kupffer cells were rinsed and placed in chambers with buffer at room temperature. Changes in fluorescence intensity of fura-2 at excitation wavelengths of 340 nm and 380 nm and emission at 520 nm were monitored in individual Kupffer cells. Each value was corrected by subtracting the system dark noise and autofluorescence, assessed by quenching fura-2 fluorescence with $Mn^{2+}$ as described previously (Hijioka, T., et al., Mol. Pharmacol. 41:435–440 (1992)). $(Ca^{2+})_i$ was determined from the equation:

$$(Ca^{2+})_i = Kd\{(R-Rmin)/(Rmax-R)\}(Fo/Fs)$$

where Fo/Fs is the ratio of fluorescent intensities evoked by 380 nm light from fura-2 pentapotassium salt in cells using a buffer containing 3 mM EGTA and 1 µM ionomycin (($Ca^{2+}$) min) or 10 mM ($Ca^{2+}$) and 1 µM ionomycin (($Ca^{2+}$) max). R is the ratio of fluorescent intensity at excitation wavelengths of 340 nm and 380 nm, and Rmax and Rmin are values of R at ($Ca^{2+}$) max and ($Ca^{2+}$) min, respectively. The values of these constants were determined at the end of each experiment. A dissociation constant of 135 nM was used (Grynkiewicz, G., M. et al. J. Biol. Chem. 260:3440–3450 (1985)).

Figure 2:
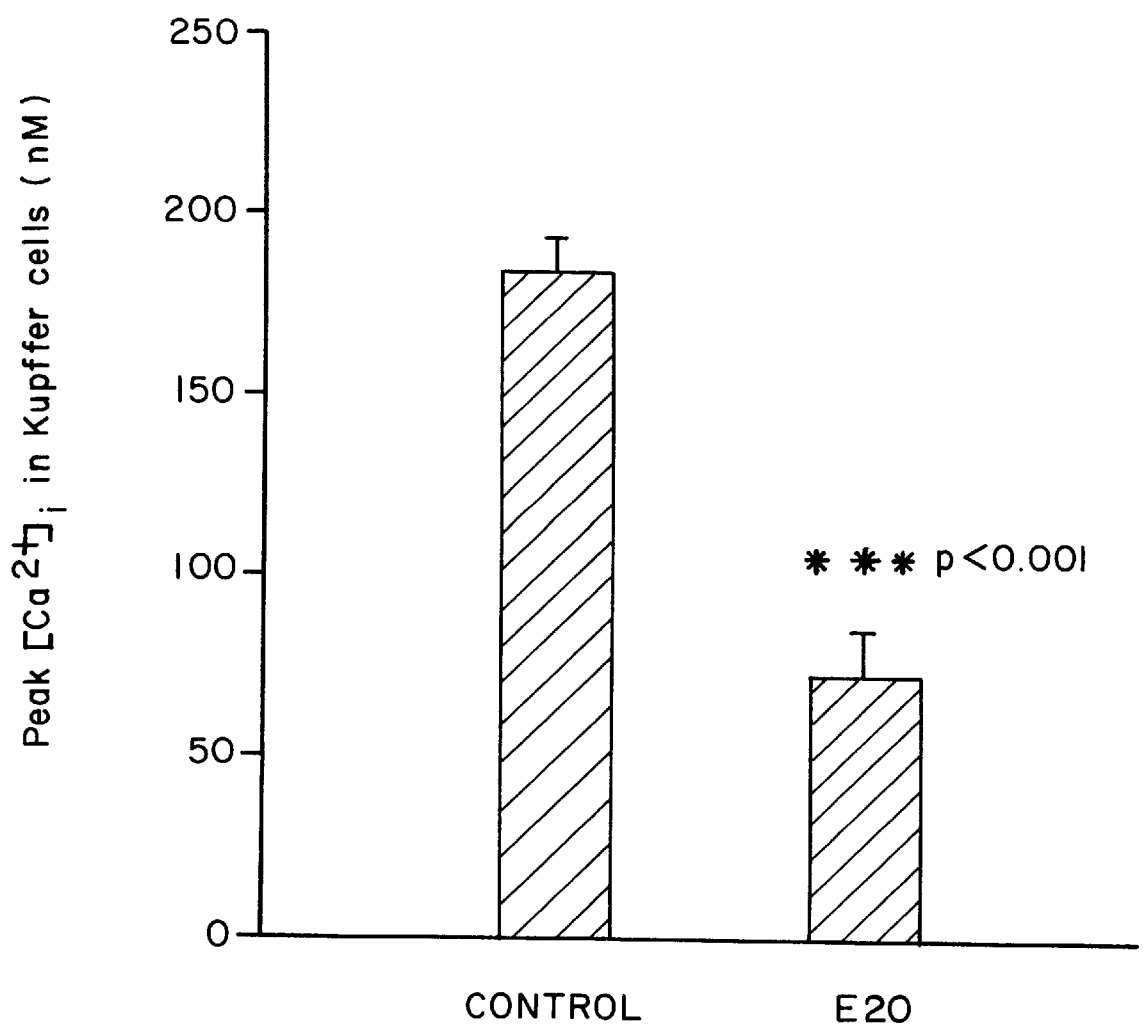
FIG. 2 shows the peak levels of $Ca^{2+}$ influx into endotoxin-treated Kupffer cells with and without pretreatment with compound E20 of the invention.

As shown in FIG. 1, addition of endotoxin (10 µg/ml) caused a clear increase in $Ca^{2+}$ in an isolated Kupffer cell. This response lasted for more than 100 seconds and was dependent on the presence of external $Ca^{2+}$. Preincubation of this preparation of Kupffer cells with compound E20 dramatically decreased this endotoxin-mediated influx of $Ca^{2+}$ (FIG. 2). indicating that cellular activation (i.e. elevation in intracellular $Ca^{2+}$) by endotoxin, is sensitive to endotoxin antagonists such as compound E20. The peak value results from FIG. 1 are presented in FIG. 2. Data shown are mean±standard error of three experiments.

Example 6

Endotoxin antagonists block the Swift Increase in Alcohol Metabolism (SIAM) induced by administration of alcohol Experimentally, a Swift Increase in Alcohol Metabolism (SIAM) characterized by an increase in basal oxygen uptake 2–3 hours following treatment with ethanol, and Kupffer cells have been implicated in this response (Yuki, T & Thurman, R. Biochem. J. 186:119–126 (1980), Casteleijn et al., J. Biol. Chem. 263: 2699–2703 (1988)).

Rats are given ethanol (5 g/kg) alone or after intravenous injection of 25 µg/kg of compound E20. After 3 hours maintenance with food and water ad libidum, rats were anaesthetized with sodium pentobarbital (50 mg/kg). The abdomen was opened, and oxygen-saturated Krebs-Henseleit-bicarbonate buffer (37° C., pH 7.4) was pumped through the liver via a cannula inserted into the portal veil. A cannula placed in the inferior vena cava allowed fluid to flow out of the liver in a non-recirculating manner as described previously (Scholz R., In: Stoffwechsel der Perfundierten Leber, (W. Staib and R. Scholz, Eds.) pp 24–34 Springer Verlag, Berlin (1968)). Oxygen concentration in the effluent perfusate was monitored with a teflon-shielded, Clark-type oxygen electrode. Samples of effluent perfusate were collected and ethanol was determined by standard enzymatic methods (Bergmeyer, H. U., Methods of Enzymatic Analysis, Academic Press, New York (1988)). Oxygen and ethanol uptake were determined from influent and effluent concentration differences, the flow rate, and the liver wet weight.

Figure 3:
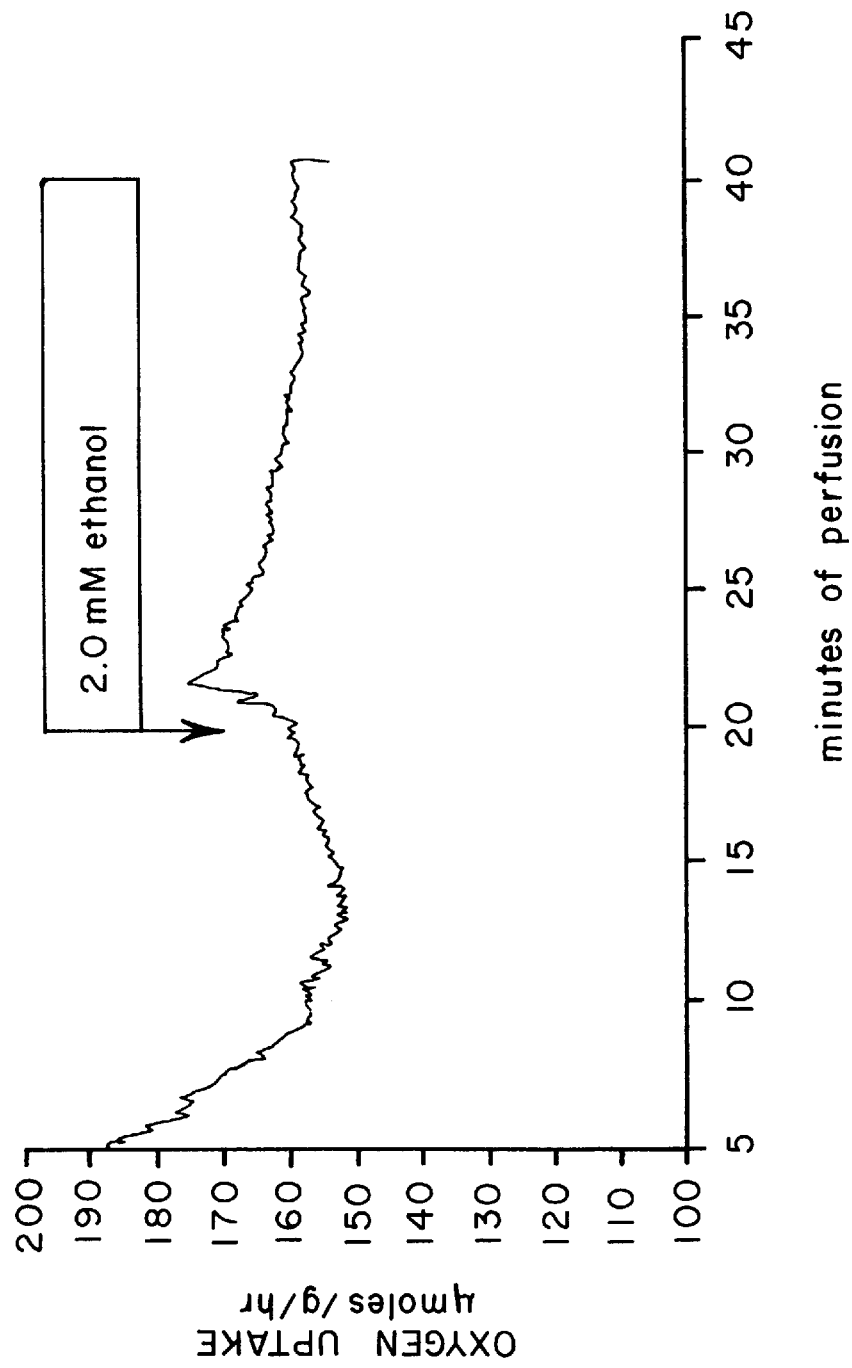
FIG. 3 shows the Swift Increase in Oxygen Metabolism in ethanol-treated rat livers.
Figure 4:
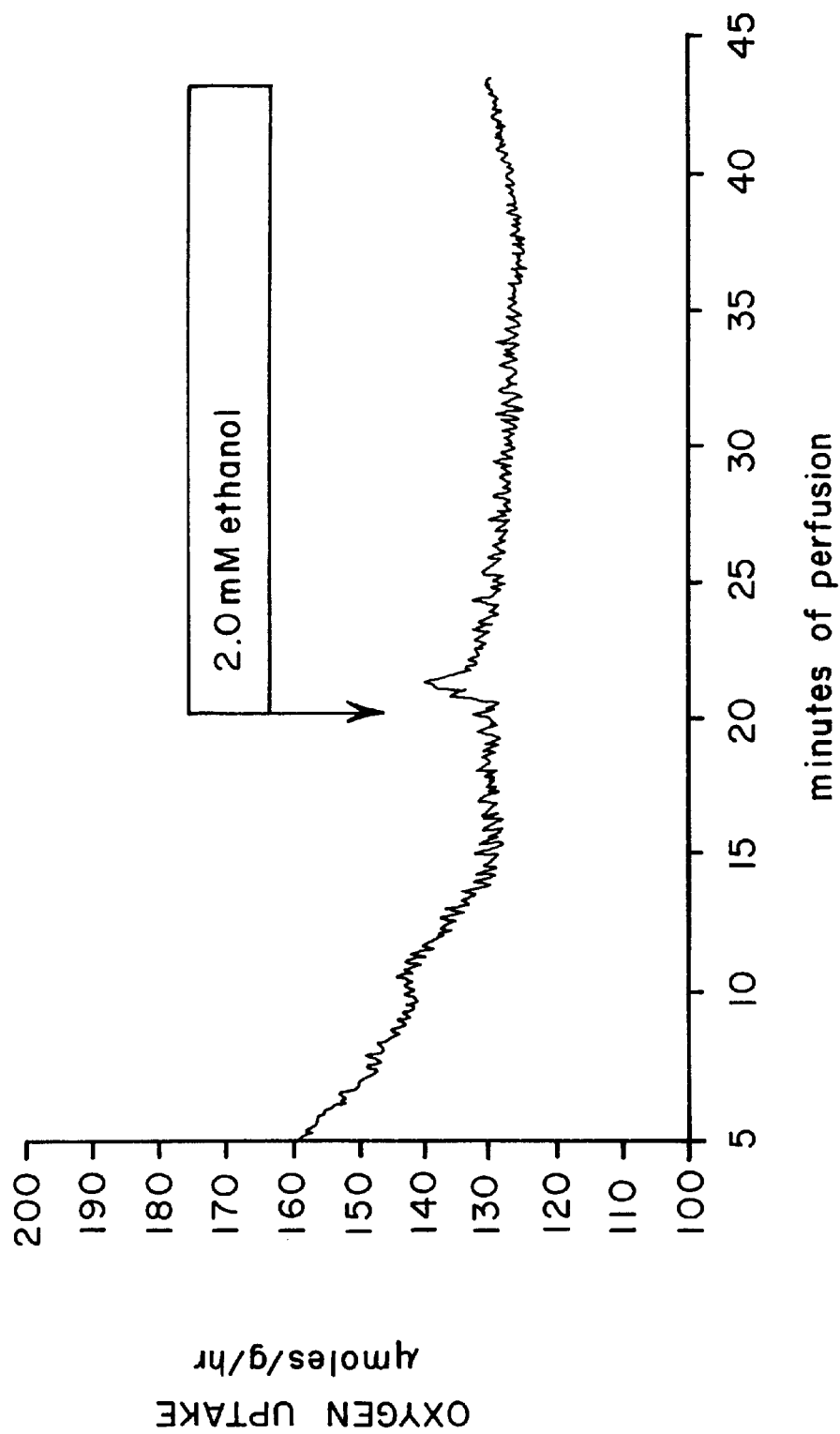
FIG. 4 shows the inhibition of the Swift Increase in Oxygen Metabolism in ethanol-treated rat livers from rats which had been pretreated with 25 μg of compound E20 of the invention.
Figure 5:
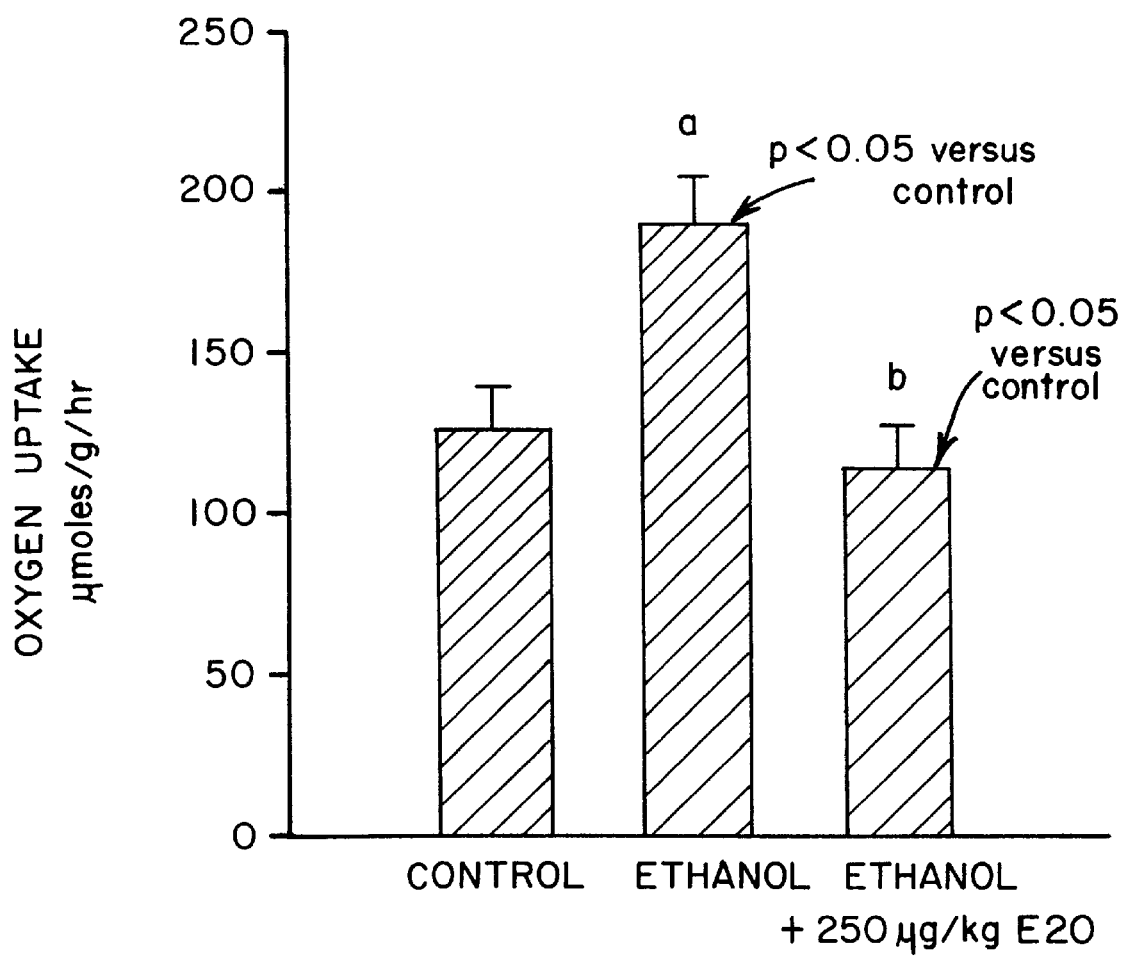
FIG. 5 shows the peak levels of oxygen metabolism in rats which were not exposed to ethanol, rats exposed to ethanol, and rats exposed to ethanol which were pretreated with compound E20 of the invention prior to exposure to ethanol.

As previously described (Yuki, T & Thurman, R. Biochem. J. 186: 119–126 (1980)), measurement of oxygen consumption by perfused livers indicates that ethanol induces a hypermetabolic state. In most cases, this increase is about 45% 3 hours after administration of ethanol. Demonstration of this hypermetabolic state by analysis of oxygen consumption is shown in FIG. 3. This enhanced oxygen consumption can be compared to that seen in control animals (~125 µmol/hour/g) as seen in FIG. 5. This stimulation of metabolism (SIAM) is blocked more than 60% by treatment of the test animal with compound E20 (25 µg/kg) prior to ethanol administration, as shown in FIGS. 3 and 4. All results are expressed as mean +/SEM. Statistical differences between means were determined using ANOVA. P<0.05 was selected prior to the study to reflect significance. These results indicate that treatment with compound E20 decreases a pathological response to alcohol, presumably through its ability to antagonize endotoxin.

Example 7

Inhibition of LPS in Human Blood

Lipid A analogs inhibited LPS-induced production of tumor necrosis factor (TNF) in human whole blood in a concentration dependent manner. Of the analogs tested, Compound E1 was found to be one of the most effective compounds. Compound E1 inhibits LPS-induced production of TNF with an $IC_{50}$ of approximately 1.5 nM. Other analogs found to inhibit LPS-induced TNF production included Compounds E2 through E21, inclusive. These compounds exhibited $IC_{50}$'s of between 1.5 nM and 159 nM.

Example 8

In vivo antagonism of LPS-induced pathophysiological responses

Other models of in video administration of endotoxin have allowed the measurement of antagonism of immune stimulation by endotoxin. For example, BCG-primed mice (Vogel et al., 1980) are utilized as an in vivo assay system for monitoring the inhibitory effects of lipid A analogs on LPS-induced TNF production and LPS-induced lethality.

Five week old male C57B1/6 mice are printed by intravenous tail vein injection with 2 mg of BCG. Ten days post-injection, *E. coli* LPS in pyrogen-free 5% glucose solution (Otsuka Pharmaceuticals, Tokyo, Japan) is administered intravenously through the tail vein of the BCG-primed mice. LPS is administered at 1–3 μg/mouse for both TNF production and mortality studies. The test compound is administered as a component of the injected LPS solution at a concentration of between 3 and 300 μg per mouse. Plasma is obtained one hour post-LPS injection, and TNF is assayed by ELISA. Mortality resulting from septic shock is recorded for 36 hours after LPS injection.

Compounds of the invention effectively suppress the production of TNF following administration of LPS. Compound E10 and compound E1 effectively inhibit TNF production in vivo in mice ($ED_{50}$=5 and 10.6 μg per mouse, respectively). Compounds E2 through E9, E20, and E21, also inhibit TNF production, with $ED_{50}$'s between 10 and 200 μg per mouse with compounds E5, E6, and E7 giving $ED_{50}$ values greater than 100 μg per mouse.

What is claimed is:

1. A method for the amelioration of at least one of the symptoms of alcoholic liver disease which comprises administering to a mammal in need of such treatment a therapeutically effective amount of a compound with the formula

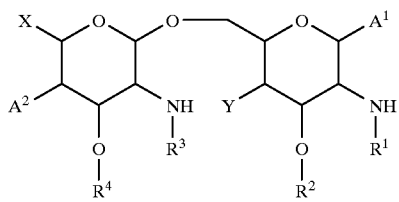

wherein at least one of $R^1$, $R^2$, $R^3$, or $R^4$ is independently selected from the group consisting of:

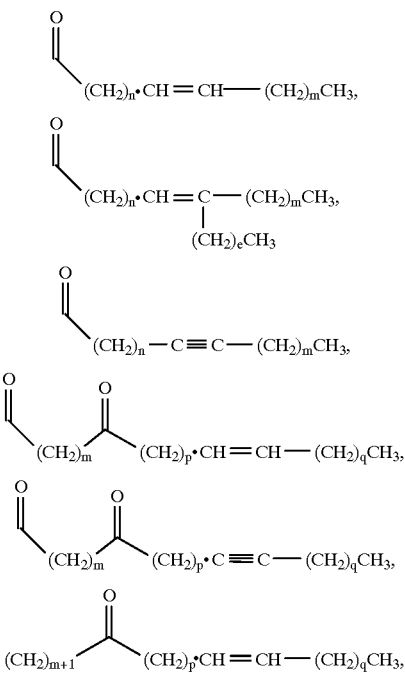

and

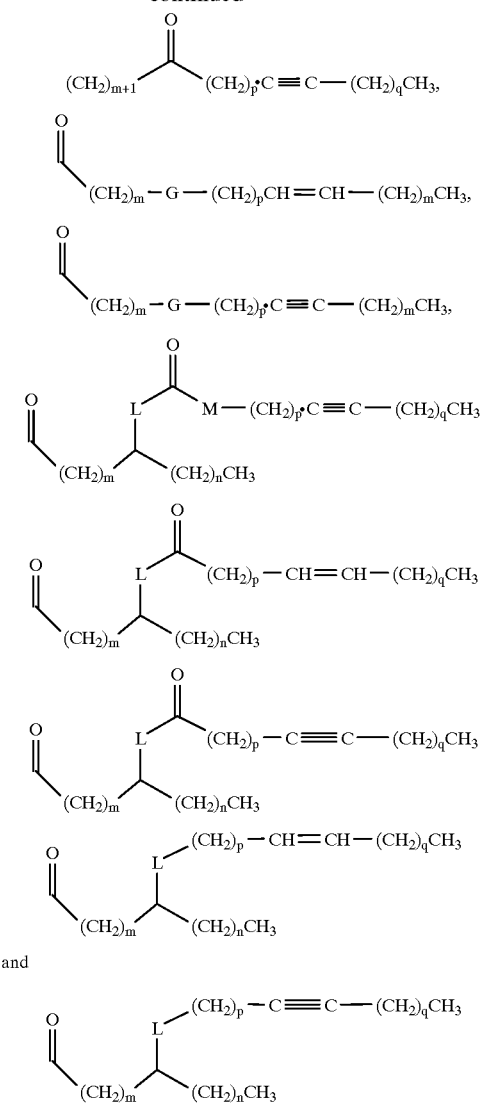

wherein each L is selected from the group consisting of O, N and C; each M is selected from the group consisting of O and N; each e, independently, is an integer between 0 and 14 inclusive; each G, independently, is N, S, SO or $SO_2$; each m, independently, is an integer between 0 and 14 inclusive; each n, independently, is an integer between 0 and 14; each p, independently, is an integer between 0 and 10, inclusive; and each q, independently, is an integer between 0 and 10 inclusive;

wherein each of the remaining $R^1$, $R^2$, $R^3$, and $R^4$, independently, is selected from the group consisting of:

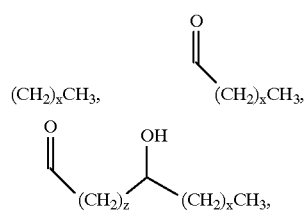

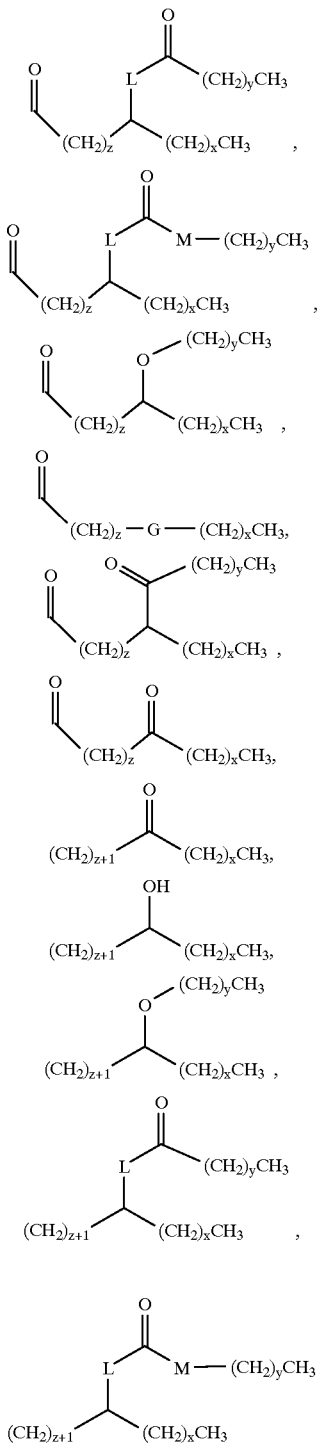

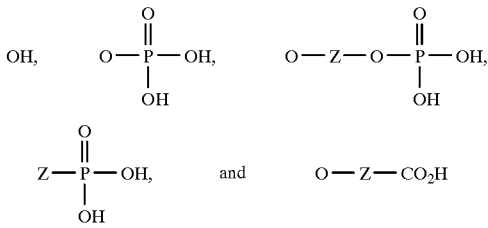

wherein each L is selected from the group consisting of O, N, and C; each M is selected from the group consisting of O and N; each x, independently, is an integer between 0 and 14 inclusive; each y, independently, is an integer between 0 and 14 inclusive; each z, independently, is an integer between 0 and 10 inclusive; and each G, independently, is selected from the group consisting of N, O, S, SO, or $SO_2$;

wherein $A^1$ and $A^2$, independently, are selected from the group consisting of

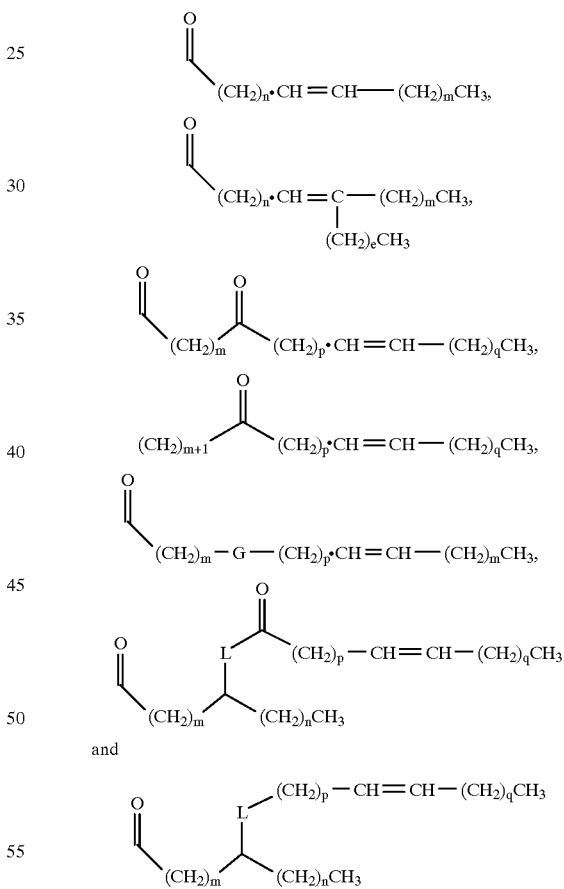

where Z is straight or branched C1 to C10 alkyl; X is selected from the group consisting of hydrogen, J',—J'—OH, —J'—O—K',—J'—O—K'—OH, and —J'—O—PO$(OH)_2$ where each J' and K', independently, is straight or branched C1 to C5 alkyl; Y is selected from the group consisting of hydrogen, hydroxy, halogen, lower alkoxy and lower acyloxy; and pharmaceutically acceptable salts thereof.

2. The method according to claim 1 wherein at least one of $R^1$, $R^2$, $R^3$, or $R^4$ is selected from the group consisting of:

wherein each L is selected from the group consisting of O, N and C; each e, independently, is an integer between 0 and 14 inclusive; each G, independently, is selected from the group consisting of N, S, SO and $SO_2$; each m, independently, is an integer between 0 and 14 inclusive; each n, independently, is an integer between 0 and 14; each p, independently, is an integer between 0 and 10, inclusive; and each q, independently, is an integer between 0 and 10 inclusive; each of the remaining $R^1$, $R^2$, $R^3$ and $R^4$, independently, is selected from the group consisting of:

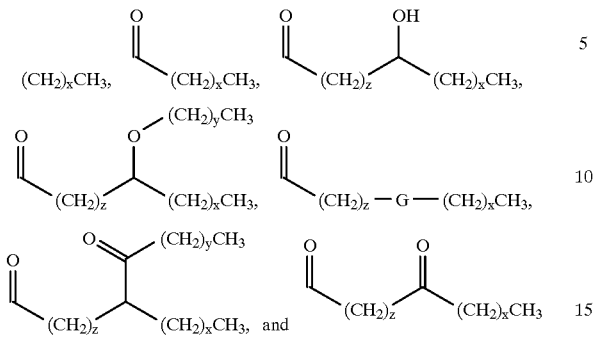

wherein each x, independently, is an integer between 0 and 14 inclusive; each y, independently, is an integer between 0 and 14 inclusive; each z, independently, is an integer between 0 and 10 inclusive; and each G, independently, is selected from the group consisting of N, O, S, SO, or $SO_2$;

wherein $A^1$ and $A^2$, independently, are selected from the group consisting of

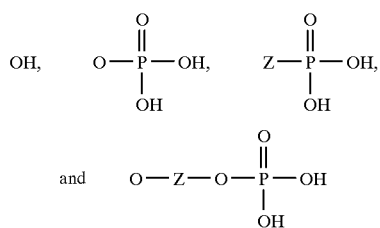

where Z is straight or branched C1 to C10 alkyl; X is selected from the group consisting of —J'—OH, —J'—O—K', —J'—O—K'—OH, and —J'—O—PO(OH)$_2$ where each J' and K', independently, is straight or branched C1 to C5 alkyl; Y is selected from the group consisting of hydroxy, halogen, lower alkoxy and lower acyloxy; and pharmaceutically acceptable salts thereof.

3. The method according to claim 2 wherein at least one of $R^1$, $R^2$, $R^3$, or $R^4$ is selected from the group consisting of:

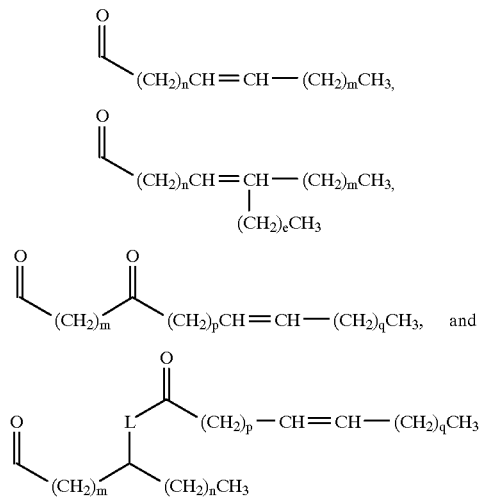

wherein L is O, N or C; each e, independently, is an integer between 0 and 14 inclusive; each m, independently, is an integer between 0 and 14 inclusive; each n, independently, is an integer between 0 and 14; each p, independently, is an integer between 0 and 10, inclusive; and each q, independently, is an integer between 0 and 10 inclusive;

wherein each of the remaining $R^1$, $R^2$, $R^3$, and $R^4$, independently, is selected from the group consisting of:

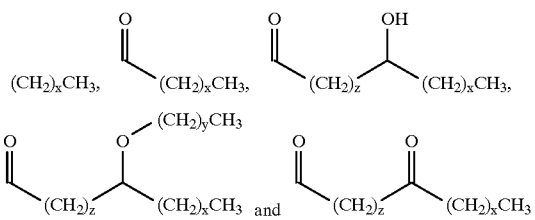

wherein each x, independently, is an integer between 0 and 14 inclusive, each y, independently, is an integer between 0 and 14 inclusive; each z, independently, is an integer between 0 and 10 inclusive; $A^1$ and $A^2$ are

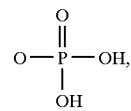

X is —J'—OH, or —J'—O—K', where each J' and K' is, independently, straight or branched C1 to C5 alkyl; Y is selected from the group consisting of hydroxy and lower acyloxy; and pharmaceutically acceptable salts thereof.

4. A method for the amelioration of at least one of the symptoms of alcoholic liver disease which comprises administering to a mammal in need of such treatment a therapeutically effective amount of a compound with the formula

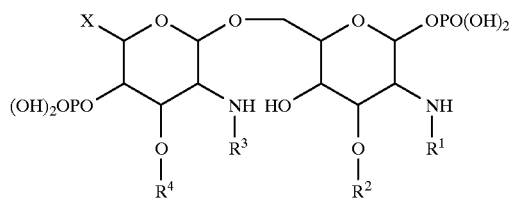

wherein X is selected from the group consisting of $CH_2OH$ and $CH_2OCH_3$;

$R^1$ is selected from the group consisting of $COCH_2CO$ $(CH_2)_{10}CH_3$, $COCH_2CH(OH)(CH_2)_{10}CH_3$, $CO(CH_2)_9$ $CH=CH(CH_2)_5CH_3$, $CO(CH_2)_{12}CH_3$, $COCH_2CH$ $(OCH_3)(CH_2)_{10}CH_3$, and $COCH_2SO(CH_2)_{10}CH_3$;

$R^2$ is selected from the group consisting of $(CH_2)_9CH_3$, $COCH_2CH(OH)(CH_2)_6CH_3$, $CH_2CH_2CH(OH)(CH_2)_6$ $CH_3$, and $CH_2CH_2CH(OH)(CH_2)_7CH_3$;

$R^3$ is selected from the group consisting of $CO(CH_2)_9$ $CH=CH(CH_2),CH_3$, $CO(CH_2)_{16}CH_3$, $COCH_2CO$ $(CH_2),OCH_3$, and $COCH_2SO(CH_2)_{10}CH_3$;

$R^4$ is selected from the group consisting of $(CH_2)_2CH$ $(OCH_3)(CH_2),CH_3$, $(CH_2)_2CH(OH)(CH_2)_6CH_3$, $(CH_2)_9CH_3$, $(CH_2)_2CH(OCH_3)(CH_2)_6CH_3$, $COCH_2CH(O-Do)(CH_2)_6CH_3$; and $CH_2CH_2CH(O-Do)(CH_2)_6CH_3$, wherein (O-Do) is $CO(CH_2)_3$ $CH=CH(CH_2)_5(CH_3)$;

and pharmaceutically acceptable salts thereof.

5. The method of claim 1 wherein said compound is selected from the group consisting of:

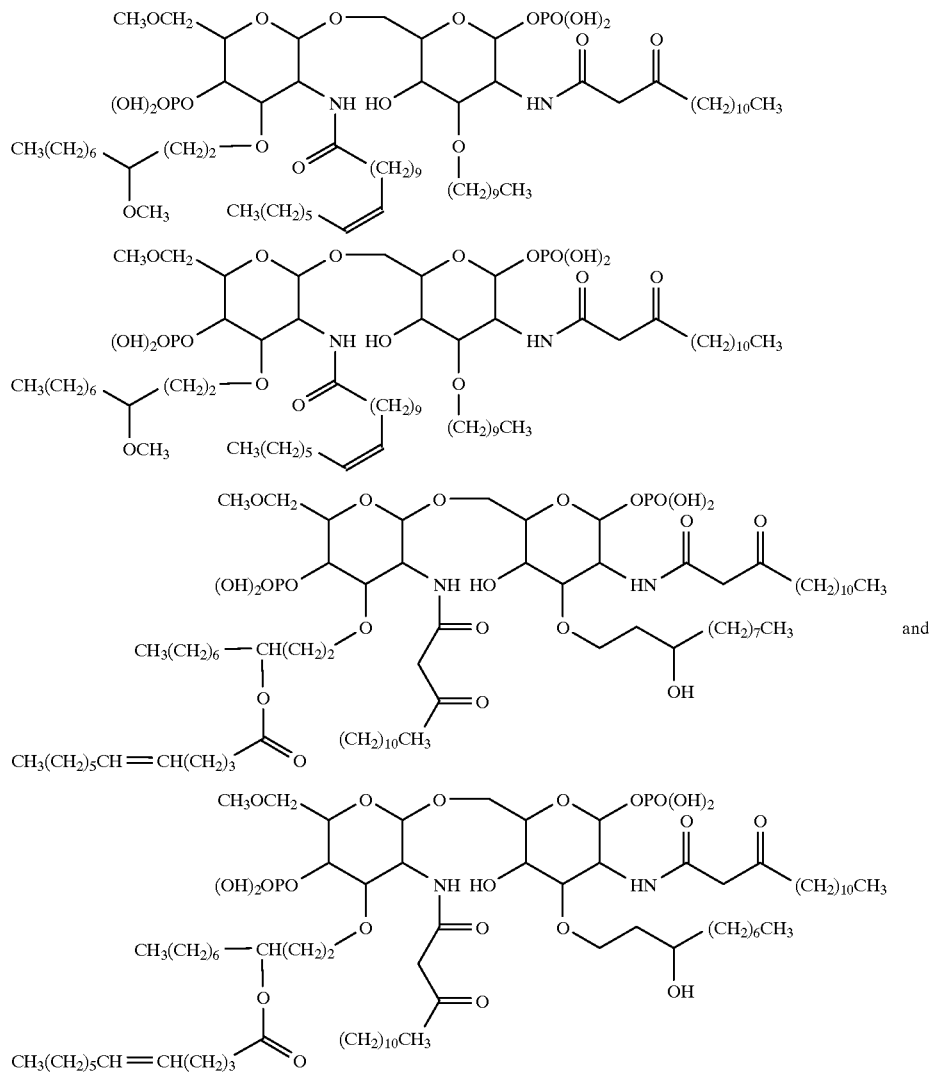

and

6. The method according to claim 1 wherein said compound is administered in an amount between about 0.01 and 50 mg per patient per day.

7. The method according to claim 4 wherein said compound is administered in an amount between about 0.01 and 50 mg per patient per day.

8. The method according to claim 5 wherein said compound is administered in an amount between about 0.01 and 50 mg per patient per day.

9. The method according to claim 1 wherein said compound is a pharmaceutically acceptable salt is selected from the group consisting of a Tris salt, a lysine salt, an ammonium salt, and a sodium salt.

10. The method according to claim 4 wherein said compound is a pharmaceutically acceptable salt is selected from the group consisting of a Tris salt, a lysine salt, an ammonium salt, and a sodium salt.

11. The method according to claim 5 wherein said compound is a pharmaceutically acceptable salt is selected from the group consisting of a Tris salt, a lysine salt, an ammonium salt, and a sodium salt.

12. The method according to claim 1 wherein said compound is administered intravenously.

13. The method according to claim 4 wherein said compound is administered intravenously.

14. The method according to claim 5 wherein said compound is administered intravenously.

15. The method according to claim 12 wherein said compound is administered in an amount between about 0.1 and 9 mg per patient per day and wherein said compound is a pharmaceutically acceptable sodium salt.

16. The method according to claim 13 wherein said compound is administered in an amount between about 0.1 and 9 mg per patient per day and wherein said compound is a pharmaceutically acceptable sodium salt.

17. The method according to claim 14 wherein said compound is administered in an amount between about 0.1 and 9 mg per patient per day and wherein said compound is a pharmaceutically acceptable sodium salt.

* * * * *

UNITED STATES PATENT AND TRADEMARK OFFICE
CERTIFICATE OF CORRECTION

PATENT NO. : 5,952,309
DATED : September 14, 1999
INVENTOR(S) : Daniel P. Rossignol et al.

It is certified that error appears in the above-indentified patent and that said Letters Patent is hereby corrected as shown below:

At column 1, line 3, insert the following:

-- Government Rights

The United States Government has a paid-up license in this invention and the right in limited circumstances to require the patent owner to license others on reasonable terms as provided by the terms of Grant No. 2-R01-AA06324-16A1, awarded by the National Institute of Alcohol Abuse (now known as the National Institute of Alcohol Abuse and Alcoholism).

Signed and Sealed this

Twentieth Day of March, 2001

Attest:

NICHOLAS P. GODICI

*Attesting Officer*   *Acting Director of the United States Patent and Trademark Office*